United States Patent
Lee et al.

(10) Patent No.: US 12,350,411 B2
(45) Date of Patent: Jul. 8, 2025

(54) ULTRAVIOLET (UV) LIGHT SOURCE INCLUDING LIGHT-EMITTING DIODE (LED) PACKAGE WITH WATERPROOF COATING LAYER

(71) Applicant: SAMSUNG ELECTRONICS CO., LTD., Suwon-si (KR)

(72) Inventors: Dongkuk Lee, Hwaseong-si (KR); Daesup Kim, Suwon-si (KR); Wooseok Jang, Hwaseong-si (KR); Hyoungcheol Cho, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 415 days.

(21) Appl. No.: 17/828,501

(22) Filed: May 31, 2022

(65) Prior Publication Data
US 2023/0141035 A1    May 11, 2023

(30) Foreign Application Priority Data
Nov. 10, 2021    (KR) .................. 10-2021-0154291

(51) Int. Cl.
*A61L 9/20*    (2006.01)
*C02F 1/32*    (2023.01)
(Continued)

(52) U.S. Cl.
CPC .............. *A61L 9/20* (2013.01); *C02F 1/325* (2013.01); *H05K 1/181* (2013.01); *H05K 5/0056* (2013.01);
(Continued)

(58) Field of Classification Search
CPC ........ H01L 33/486; H01L 33/62; H01L 33/56; H01L 33/06; H01L 33/483; H01L 24/16;
(Continued)

(56) References Cited

U.S. PATENT DOCUMENTS

| | | | |
|---|---|---|---|
| 6,372,608 B1 | 4/2002 | Shimoda et al. | |
| 6,645,830 B2 | 11/2003 | Shimoda et al. | |

(Continued)

FOREIGN PATENT DOCUMENTS

| | | | |
|---|---|---|---|
| CN | 213048346 U | 4/2021 | |
| JP | 2015-016418 A | * 1/2015 | .............. B01J 35/00 |

(Continued)

OTHER PUBLICATIONS

Communication dated Aug. 21, 2024, issued by the German Patent and Trademark Office in German Patent Application No. 102022117559.6.

*Primary Examiner* — Peter Bradford
*Assistant Examiner* — Ryan T. Fortin
(74) *Attorney, Agent, or Firm* — Sughrue Mion, PLLC

(57) ABSTRACT

An ultraviolet (UV) light source includes: a substrate coupled to an upper housing; a light-emitting diode (LED) package on the substrate; and a waterproof coating layer on at least a portion of the substrate, wherein the LED package includes: an LED chip configured to generate UV light; and a transparent layer including a lower surface facing the LED chip, an upper surface opposite to the lower surface, and a lateral surface connecting the upper surface to the lower surface, wherein at least a portion of the upper surface of the transparent layer is exposed from the waterproof coating layer, and the transparent layer is configured to directly contact a sterilization-target fluid.

18 Claims, 17 Drawing Sheets

(51) Int. Cl.
*H01L 23/00* (2006.01)
*H05K 1/18* (2006.01)
*H05K 5/00* (2025.01)
*H10H 20/825* (2025.01)
*H10H 20/85* (2025.01)
*H10H 20/857* (2025.01)

(52) U.S. Cl.
CPC ...... *H10H 20/8506* (2025.01); *H10H 20/857* (2025.01); *C02F 2201/3222* (2013.01); *C02F 2303/04* (2013.01); *H01L 24/16* (2013.01); *H01L 2224/16227* (2013.01); *H05K 2201/10106* (2013.01); *H05K 2201/10977* (2013.01); *H10H 20/825* (2025.01)

(58) Field of Classification Search
CPC .......... H01L 2224/16227; H05K 1/181; H05K 5/0056; H05K 2201/10106; H05K 2201/10977; A61L 2/10; A61L 9/20; C02F 1/325; C02F 2201/3222; C02F 2303/04; F21K 9/66; F21V 15/01; F21V 19/003; F21V 31/005; F21V 33/0064; H10H 20/8506; H10H 20/857; H10H 20/825
See application file for complete search history.

(56) References Cited

U.S. PATENT DOCUMENTS

| | | | |
|---|---|---|---|
| RE38,466 E | 3/2004 | Inoue et al. |
| 6,818,465 B2 | 11/2004 | Biwa et al. |
| 6,818,530 B2 | 11/2004 | Shimoda et al. |
| 6,858,081 B2 | 2/2005 | Biwa et al. |
| 6,967,353 B2 | 11/2005 | Suzuki et al. |
| 7,002,182 B2 | 2/2006 | Okuyama et al. |
| 7,084,420 B2 | 8/2006 | Kim et al. |
| 7,087,932 B2 | 8/2006 | Okuyama et al. |
| 7,154,124 B2 | 12/2006 | Han et al. |
| 7,208,725 B2 | 4/2007 | Sherrer et al. |
| 7,288,758 B2 | 10/2007 | Sherrer et al. |
| 7,319,044 B2 | 1/2008 | Han et al. |
| 7,501,656 B2 | 3/2009 | Han et al. |
| 7,709,857 B2 | 5/2010 | Kim et al. |
| 7,759,140 B2 | 7/2010 | Lee et al. |
| 7,781,727 B2 | 8/2010 | Sherrer et al. |
| 7,790,482 B2 | 9/2010 | Han et al. |
| 7,940,350 B2 | 5/2011 | Jeong |
| 7,959,312 B2 | 6/2011 | Yoo et al. |
| 7,964,881 B2 | 6/2011 | Choi et al. |
| 7,985,976 B2 | 7/2011 | Choi et al. |
| 7,994,525 B2 | 8/2011 | Lee et al. |
| 8,008,683 B2 | 8/2011 | Choi et al. |
| 8,013,352 B2 | 9/2011 | Lee et al. |
| 8,049,161 B2 | 11/2011 | Sherrer et al. |
| 8,129,711 B2 | 3/2012 | Kang et al. |
| 8,179,938 B2 | 5/2012 | Kim |
| 8,263,987 B2 | 9/2012 | Choi et al. |
| 8,324,595 B2 | 12/2012 | Takahashi et al. |
| 8,324,646 B2 | 12/2012 | Lee et al. |
| 8,399,944 B2 | 3/2013 | Kwak et al. |
| 8,432,511 B2 | 4/2013 | Jeong |
| 8,459,832 B2 | 6/2013 | Kim |
| 8,502,242 B2 | 8/2013 | Kim |
| 8,536,604 B2 | 9/2013 | Kwak et al. |
| 8,735,931 B2 | 5/2014 | Han et al. |
| 8,766,295 B2 | 7/2014 | Kim |
| 9,233,857 B2 | 1/2016 | Nikamoto |
| 10,260,734 B2 | 4/2019 | Kim et al. |
| 10,654,729 B2 | 5/2020 | Mochizuki et al. |
| 10,736,980 B2 | 8/2020 | Mochizuki et al. |
| 2015/0070909 A1* | 3/2015 | Jung ................ H01L 33/54 362/362 |
| 2017/0229614 A1* | 8/2017 | Kim ................. H01L 33/52 |
| 2020/0041115 A1 | 2/2020 | Kim et al. |
| 2020/0223717 A1* | 7/2020 | Jung ................. C02F 1/32 |
| 2021/0008241 A1* | 1/2021 | Jeong ............... C02F 1/325 |
| 2021/0393817 A1* | 12/2021 | Jeong ............... A61L 2/10 |

FOREIGN PATENT DOCUMENTS

| | | |
|---|---|---|
| KR | 10-2017-0000216 A | 1/2017 |
| KR | 10-2018-0130822 A | 12/2018 |
| KR | 10-2020-0042824 A | 4/2020 |
| KR | 10-2020-0045247 A | 5/2020 |
| KR | 10-2020-0052184 A | 5/2020 |

\* cited by examiner

ULTRAVIOLET (UV) LIGHT SOURCE INCLUDING LIGHT-EMITTING DIODE (LED) PACKAGE WITH WATERPROOF COATING LAYER

CROSS-REFERENCE TO THE RELATED APPLICATION

This application is based on and claims priority from Korean Patent Application No. 10-2021-0154291, filed on Nov. 10, 2021, in the Korean Intellectual Property Office, the disclosure of which is incorporated by reference herein in its entirety.

BACKGROUND

Embodiments of the present disclosure relate to an ultraviolet (UV) light source and a method of manufacturing the UV light source.

Light-emitting diode (LED) chips and LED packages including LED chips have several advantages, such as low power consumption, high brightness, long lifespan, and the like, and thus, areas of use thereof as light sources have gradually increased.

Recently, due to the pandemic situation that has been going on since 2020, there is an increasing interest in UV LEDs used for sterilization and disinfection of air, water, or the like.

According to the related art, there has been a large number of applications using mercury UV lamps. UV LEDs, which have been recently developed, have a smaller volume, lighter weight, more compact structures, and five or more times longer lifespan than mercury UV lamps. UV LEDs have more freedom with regard to emission wavelengths, lower heat emission, and better energy efficiency than mercury lamps. In addition, UV LEDs do not generate ozone, which is harmful to humans and the environment, and do not require heavy metals such as mercury or the like.

SUMMARY

Embodiments of the present disclosure provide an ultraviolet (UV) light source, which has improved heat dissipation and light extraction efficiency, and a method of manufacturing the UV light source.

According to embodiments of the present disclosure, an ultraviolet (UV) light source is provided. The UV light source includes: a lower housing; an upper housing coupled to the lower housing, the upper housing including a plate portion and a sidewall protruding from the plate portion; a substrate coupled to the upper housing; a light-emitting diode (LED) package on the substrate; a waterproof coating layer on at least a portion of the substrate; and a first waterproof layer between the waterproof coating layer and the upper housing. The LED package includes: an LED chip configured to generate UV light; and a transparent layer including a lower surface facing the LED chip, an upper surface opposite to the lower surface, and a lateral surface connecting the upper surface to the lower surface, wherein at least a portion of the upper surface of the transparent layer is exposed from the waterproof coating layer, and wherein the transparent layer is configured to directly contact a sterilization-target fluid.

According to embodiments of the present disclosure, a UV light source is provided. The UV light source includes: an upper housing including a plate portion and a sidewall protruding from the plate portion; a substrate coupled to the upper housing; a light-emitting diode (LED) chip on the substrate and including a transparent layer; a waterproof coating layer on the substrate and at least a portion of the LED chip; and a first waterproof layer between the waterproof coating layer and the upper housing, wherein at least a portion of an upper surface of the transparent layer is exposed from the waterproof coating layer, such that the LED chip is configured to generate UV light that is directly transferred to a sterilization-target fluid without passing through the waterproof coating layer.

According to embodiments of the present disclosure, a UV light source is provided. The UV light source includes: an upper housing including a plate portion and a sidewall protruding from the plate portion; a substrate coupled to the upper housing; a light-emitting diode (LED) package on an upper surface of the substrate and including an LED chip configured to generate UV light; a waterproof coating layer on at least a portion of the upper surface of the substrate; a first waterproof layer between the substrate and the upper housing; and a connector connected to the substrate and providing a path for drive power to the LED chip. The LED package further includes: a base layer including a plate portion, which is overlapped with a lower surface of the LED chip, and a dam portion, which is overlapped with a lateral surface of the LED chip; and a transparent layer on the dam portion of the base layer, the transparent layer including a lower surface facing the LED chip, an upper surface opposite to the lower surface of the transparent layer, and a lateral surface connecting the upper surface of the transparent layer to the lower surface of the transparent layer.

According to embodiments of the present disclosure, a method of manufacturing a UV light source is provided. The method includes: mounting a light-emitting diode (LED) package on a first side of a substrate; providing a waterproof coating layer on the substrate and the LED package, by providing a waterproof material and curing the waterproof material; coupling the substrate, on which the LED package is mounted, to an upper housing such that a waterproof layer is arranged between the upper housing and the substrate; providing a molding layer on a second side of the substrate, opposite to the first side; and coupling the upper housing to a lower housing.

BRIEF DESCRIPTION OF THE DRAWINGS

Embodiments of the present disclosure will be more clearly understood from the following detailed description taken in conjunction with the accompanying drawings in which.

DETAILED DESCRIPTION OF THE EMBODIMENTS

Figure 1:
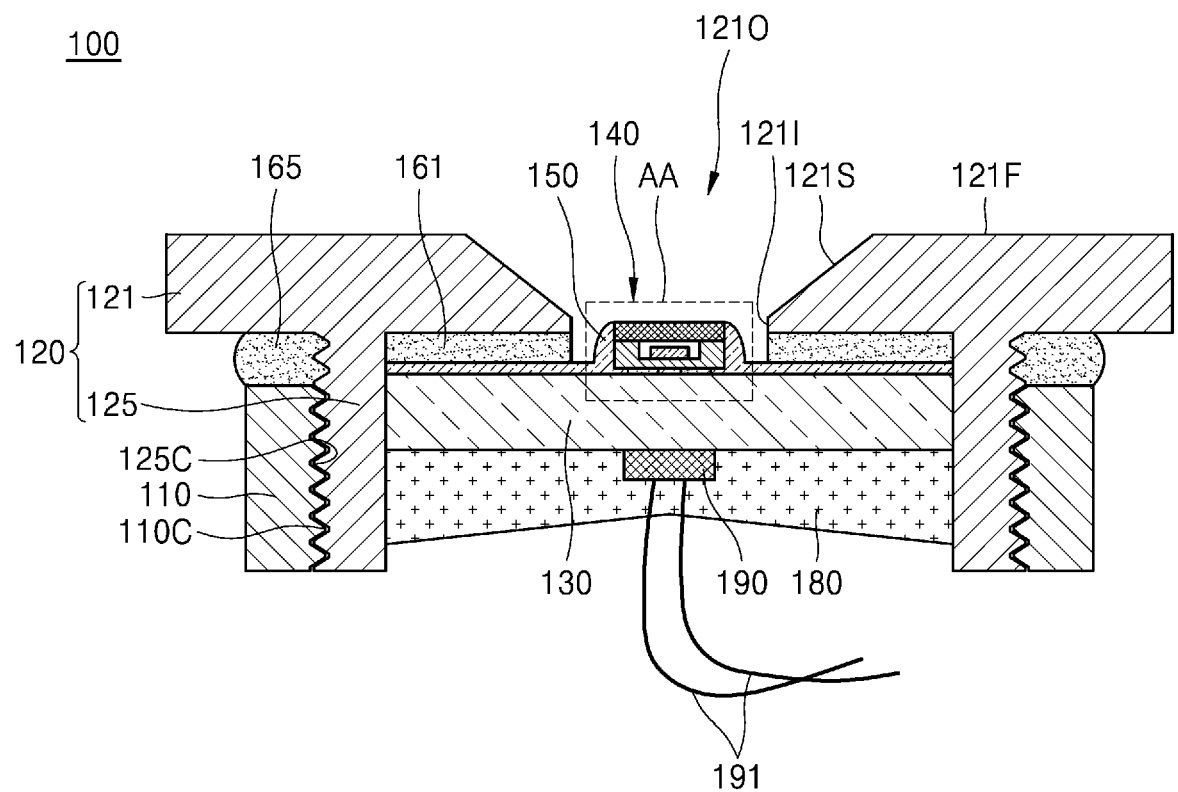
FIG. 1 is a cross-sectional view of an ultraviolet (UV) light source according to example embodiments.

Hereinafter, non-limiting example embodiments of the present disclosure will be described in detail with reference to the accompanying drawings. Like components are denoted by like reference numerals throughout the specification, and repeated descriptions thereof are omitted.

It will be understood that when an element or layer is referred to as being "over," "above," "on," "below," "under," "beneath," "connected to" or "coupled to" another element or layer, it can be directly over, above, on, below, under, beneath, connected or coupled to the other element or layer or intervening elements or layers may be present. In contrast, when an element is referred to as being "directly over," "directly above," "directly on," "directly below," "directly under," "directly beneath," "directly connected to" or "directly coupled to" another element or layer, there are no intervening elements or layers present.

FIG. 1 is a cross-sectional view illustrating an ultraviolet (UV) light source 100 according to example embodiments.

Figure 2:
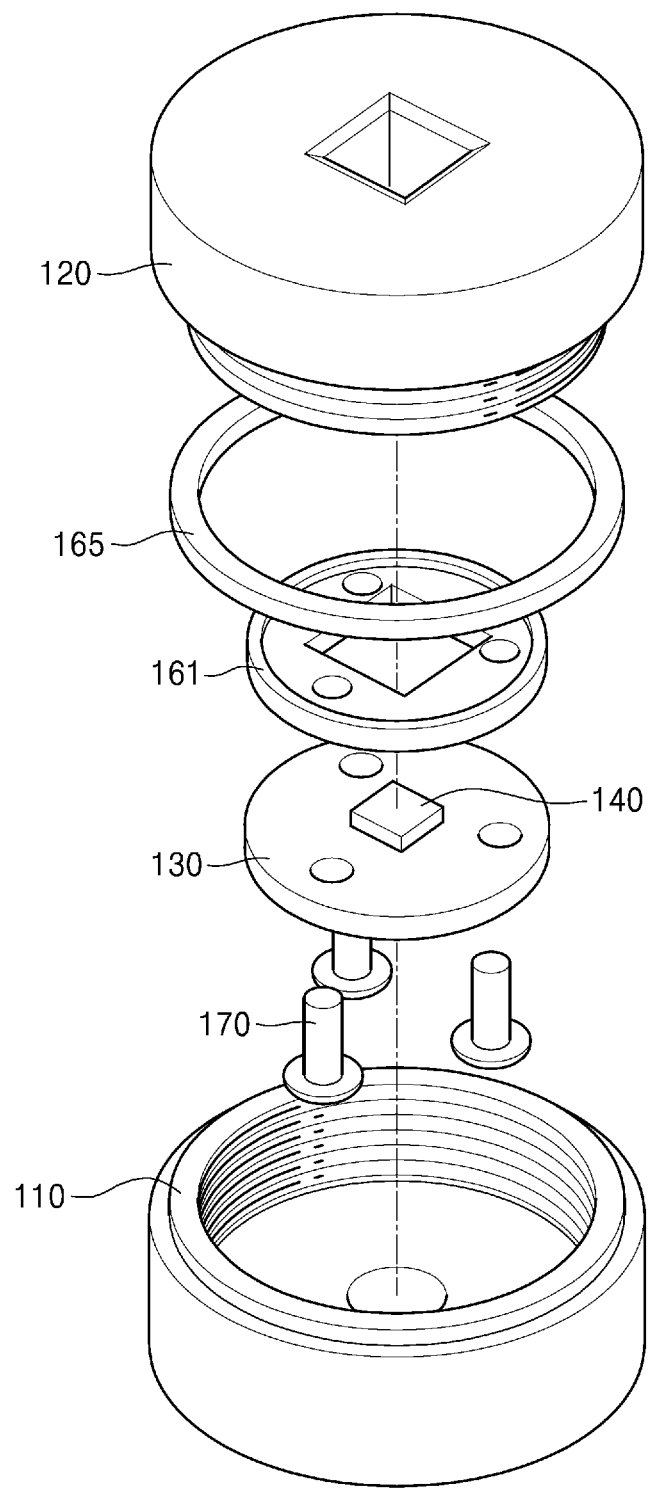
FIG. 2 is an exploded perspective view of the UV light source of FIG. 1.

FIG. 2 is an exploded perspective view of the UV light source 100 of FIG. 1.

Figure 3:
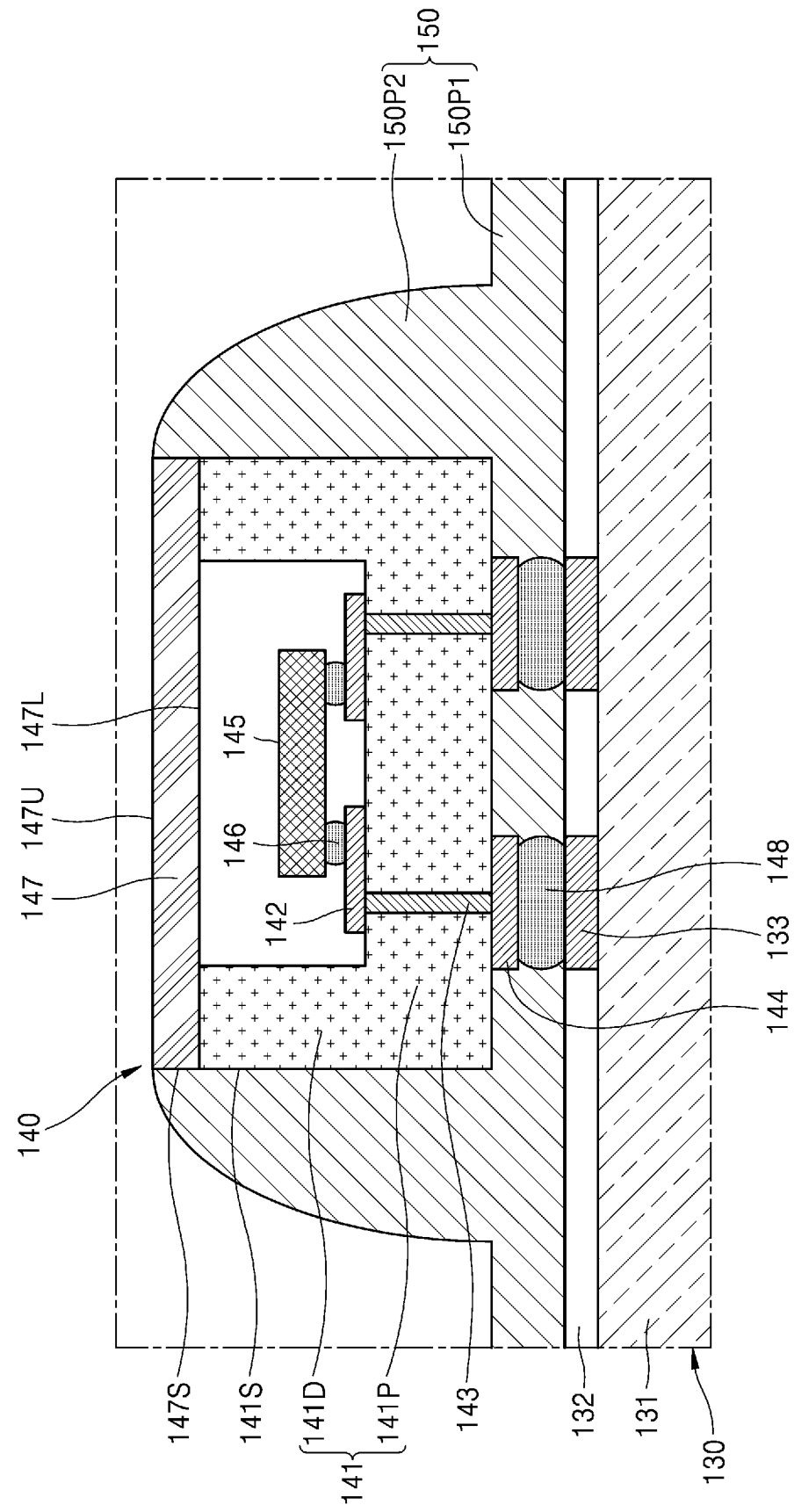
FIG. 3 is a partially enlarged cross-sectional view of a region AA of FIG. 1.

FIG. 3 is a partially enlarged cross-sectional view of a region AA of FIG. 1.

Referring to FIGS. 1 to 3, the UV light source 100 may include a lower housing 110, an upper housing 120, a substrate 130, a light-emitting diode (LED) package 140, a waterproof coating layer 150, a first waterproof layer 161, a second waterproof layer 165, securing devices 170, a molding layer 180, and a connector 190.

According to example embodiments, the UV light source 100 may be configured to generate and emit UV light. According to example embodiments, the UV light source 100 may be configured to generate and emit UV light in a narrow wavelength band. The UV light source 100 generates only UV light in a narrow wavelength band, which is used for disinfection and sterilization, and thus, energy efficiency of the UV light source 100 may be improved.

As a non-limiting example, the UV light source 100 may generate UVC light. As a non-limiting example, a wavelength of light generated by the UV light source 100 may range from about 100 nm to about 280 nm. The UV light source 100 may generate UVA light having a wavelength of about 315 nm to about 400 nm or generate UVB light having a wavelength of about 280 nm to about 320 nm.

According to example embodiments, the UV light source 100 may be configured to sterilize and disinfect a fluid such as air and water. According to example embodiments, the UV light source 100 may remove viruses, bacteria, and the like, which are included in a sterilization-target fluid, by generating UV light and irradiating the sterilization-target fluid with the UV light.

The lower housing 110 may be coupled to the upper housing 120. The lower housing 110 may protect the substrate 130 and the LED package 140. The lower housing 110 and the upper housing 120 may be coupled to a container, such as a water tank or the like, for storing a fluid that is a sterilization target.

The lower housing 110 may have a hollow cylinder shape. An inner surface of the lower housing 110 may include a first fastening structure 110C. The first fastening structure 110C may include screw threads or spiral grooves. The lower housing 110 may discharge heat generated according to an operation of the UV light source 100.

The lower housing 110 and the upper housing 120 that is described below may each include a metal material or a nonmetal material. As a non-limiting example, the metal material may include at least one from among chromium (Cr), molybdenum (Mo), nickel (Ni), aluminum (Al), and stainless steel. As a non-limiting example, the nonmetal material may include one of glass, quartz, sapphire, polycarbonate, polyamide, polypropylene (PP), polyethylene (PE), polycarbonate (PC), polybutylene terephthalate (PBT), polyoxymethylene (POM, also known as polyacetal), a polyphenylene oxide (PPO) resin, and a modified PPO resin. Here, the modified PPO resin includes a resin obtained by mixing PPO with a polystyrene or polyamide resin, has heat resistance, and stably maintains material properties even at a low temperature.

The upper housing 120 may include a plate portion 121 and a sidewall 125. The upper housing 120 may be coupled to the lower housing 110. The substrate 130 and the LED package 140 may be arranged in an internal space defined by the plate portion 121 and the sidewall 125 of the upper housing 120.

The plate portion 121 may include a flat surface 121F, which is substantially a plane, an inner circumferential surface 121I, which defines an opening 121O exposing the LED package 140, and an inclined surface 121S, which connects the inner circumferential surface 121I to the flat surface 121F. The flat surface 121F may horizontally surround the opening 121O.

The area of the opening 121O may be greater than the area of the LED package 140. Accordingly, the opening 121O may expose an entire upper surface 147U of a transparent layer 147 of the LED package 140. A planar shape of the opening 121O may be similar to a planar shape of the LED package 140. For example, when the planar shape of the LED package 140 is approximately rectangular, the planar shape of the opening 121O may be approximately rectangular.

The inclined surface 121S may improve a light extraction efficiency of the UV light source 100 by reflecting light emitted through the opening 121O.

The sidewall 125 may protrude from the plate portion 121. As a non-limiting example, the sidewall 125 may have an approximately cylindrical shape. A fastening structure 125C may be provided to an inner surface of the sidewall 125. The fastening structure 125C may include screw threads or spiral grooves. The fastening structure 125C may be coupled to the first fastening structure 110C.

The substrate 130 may be coupled to the upper housing 120. The substrate 130 may be secured to the upper housing 120 by at least one of the securing devices 170, such as a bolt or the like. The securing devices 170 may be secured to the upper housing 120 in a press fit manner through the substrate 130 and the first waterproof layer 161.

According to example embodiments, the substrate 130 may be a printed circuit board (PCB). The substrate 130 may be designed by, for example, a surface mounting technique. The substrate 130 may include a substrate base 131, conductive patterns including pads 133, and an insulating layer 132 surrounding the conductive patterns.

The substrate base 131 may include aluminum. Because the substrate base 131 including aluminum has high heat conductivity, the substrate base 131 including aluminum may effectively discharge heat generated by the LED package 140. Accordingly, an operating temperature of the UV light source 100 may be decreased, and the lifespan of the UV light source 100 may be increased. In addition, because the LED package 140 does not require a separate radiator, the volume of the UV light source 100 may be reduced, and the mechanical strength of the UV light source 100 may be improved. The substrate base 131 may have, but is not limited to, a coefficient of thermal expansion of about 20.0 parts per million (ppm) or more.

According to example embodiments, the conductive patterns including the pads 133 may each include a conductive material such as copper or the like. The insulating layer 132 may include, for example, a photosensitive resist. One of the pads 133 may be connected to a cathode of the LED package 140, and another one of the pads 133 may be connected to an anode of the LED package 140.

According to example embodiments, the pads 133 may provide paths for supplying operating power and signals to the LED package 140. According to example embodiments, the pads 133 may provide paths for discharging heat generated by the LED package 140.

The LED package 140 may be mounted on the substrate 130. A plurality of the LED package 140 may be secured and connected to the substrate 130 by external connection solders 148. The external connection solders 148 may be respectively connected to the pads 133.

Heretofore, although the substrate 130 including the substrate base 131 made of aluminum has been described, this is merely a non-limiting example and does not limit the scope of the present disclosure in any way.

Those of ordinary skill in the art would also recognize, based on descriptions made herein, that the present disclosure also includes an embodiment where the substrate 130 is a metal-core PCB (MCPCB) including copper, an embodiment where the substrate 130 is a flexible PCB that is flexible and easily transformable into various shapes, and an embodiment where the substrate 130 is a general FR4-type PCB.

The LED package 140 may be mounted on the substrate 130. The LED package 140 may include a base layer 141, pads 142, through-electrodes 143, external connection pads 144, an LED chip 145, solders 146, and a transparent layer 147.

As a non-limiting example, the LED package 140 may be mounted on the substrate 130 by the external connection solders 148. However, embodiments of the present disclosure are not limited thereto, and the LED package 140 may be mounted on the substrate 130 by eutectic bonding, and in this case, the external connection solders 148 may be omitted.

The base layer 141 may include, for example, an insulating material such as a ceramic material. The ceramic material may include low temperature co-fired ceramic (LTCC) or high temperature co-fired ceramic (HTCC). As a non-limiting example, the base layer 141 may include AlN, $Al_2O_3$, and the like. According to example embodiments, the base layer 141 may have a high heat conductivity of 140 W/m·K or more. Accordingly, the base layer 141 may effectively discharge heat generated by the LED chip 145.

The base layer 141 may include a plate portion 141P, which covers a lower surface of the LED chip 145, and a dam portion 141D, which covers a lateral surface of the LED chip 145. According to example embodiments, the base layer 141 may improve the light extraction efficiency of the UV light source 100 by reflecting light generated by the LED chip 145.

The pads 142, the through-electrodes 143, the external connection pads 144, and the external connection solders 148 may provide electrical paths for the LED chip 145. According to example embodiments, signals and power for driving the LED chip 145 may be provided through the pads 142, the through-electrodes 143, the external connection pads 144, and the external connection solders 148.

The pads 142 may be provided onto an upper surface of the base layer 141. The external connection pads 144 may be provided onto the lower surface of the base layer 141. The through-electrodes 143 may pass through the base layer 141 and be connected to the respective pads 142 and the respective external connection pads 144. One of the pads 142 may be connected to an anode of the LED chip 145, and another one of the pads 142 may be connected to a cathode of the LED chip 145.

The LED chip 145 may be coupled to the base layer 141 by eutectic bonding. The LED chip 145 may be coupled to the pads 142 by the solders 146.

The transparent layer 147 may be arranged on the dam portion 141D of the base layer 141. The transparent layer 147 may include a material having high transmittance with respect to ultraviolet light including UVC. According to example embodiments, the transparent layer 147 may include glass, quartz, or the like.

According to example embodiments, the transparent layer 147 may be secured to the dam portion 141D of the base layer 141. In one example, a waterproof bonding agent may be provided between the transparent layer 147 and the dam portion 141D of the base layer 141. In another example, the transparent layer 147 may be coupled to the dam portion 141D of the base layer 141 by a hermetic seal. The hermetic seal may be provided by fusion bonding between the transparent layer 147 and the dam portion 141D of the base layer 141. The hermetic seal may prevent a fluid such as water from flowing between the transparent layer 147 and the base layer 141.

A lower surface 147L of the transparent layer 147 may face the LED chip 145. An upper surface 147U of the transparent layer 147 may be opposite to the lower surface 147L of the transparent layer 147. The upper surface 147U of the transparent layer 147 may contact a sterilization-target fluid. A lateral surface 147S of the transparent layer 147 may connect the upper surface 147U to the lower surface 147L.

Hereinafter, a structure of the LED chip 145 will be described in more detail with reference to FIG. 4.

Figure 4:
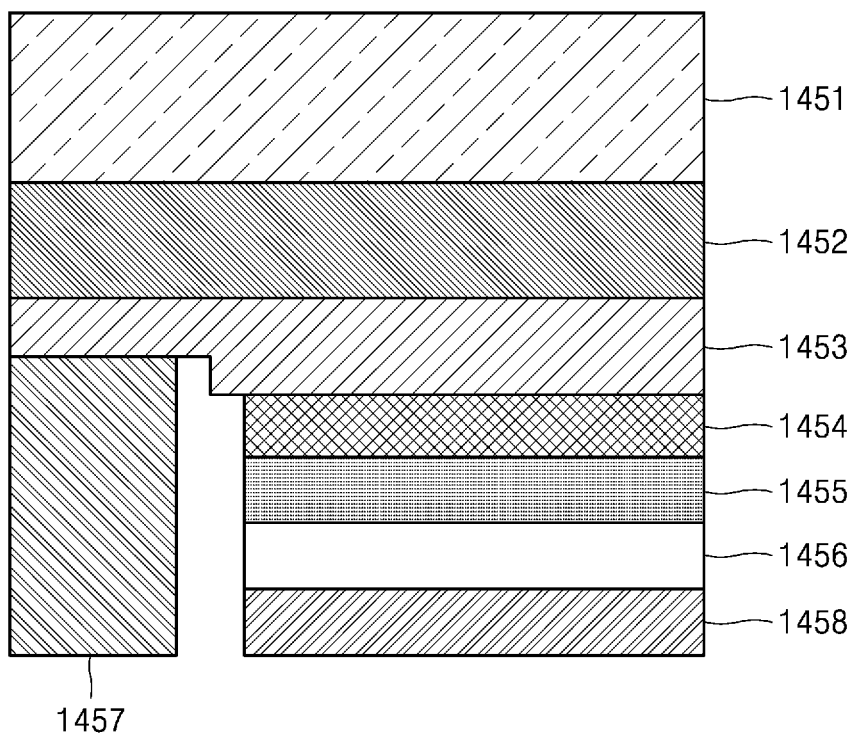
FIG. 4 is a cross-sectional view of a light-emitting diode (LED) chip.

FIG. 4 is a cross-sectional view illustrating the LED chip 145.

Referring to FIG. 4, the LED chip 145 may include a transparent layer 1451, a buffer layer 1452, a first conductivity-type nitride semiconductor layer 1453, an active layer 1454, second conductivity-type nitride semiconductor layers 1455 and 1456, a first electrode 1457, and a second electrode 1458.

The transparent layer 1451 may be transparent with respect to light generated by the LED chip 145. As a non-limiting example, the transparent layer 1451 may include sapphire and may be a portion of a growth substrate for forming the LED chip 145. In the transparent layer 1451 for growth including sapphire, a sapphire substrate is a crystal having electrical insulating properties and having hexa-rhombo R3c symmetry, respectively has lattice constants of 13.001 Å and 4.758 Å in c-axis and a-axis directions, and has a C (0001) plane, an A (1120) plane, an R (1102) plane, and the like. In this case, a C-plane of sapphire substrate allows the growth of a nitride thin layer thereon and is mainly used as a substrate for nitride growth due to stability thereof at high temperature.

In another example, the transparent layer 1451 may be provided separately from the growth of a nitride semiconductor layer, and the LED chip 145 may be manufactured based on a growth substrate including a material such as Si, SiC, $MgAl_2O_4$, MgO, $LiAlO_2$, $LiGaO_2$, GaN, or the like.

The buffer layer 1452 may be arranged on the transparent layer 1451. The buffer layer 1452 may alleviate lattice defects of the first conductivity-type nitride semiconductor layer 1453, the active layer 1454, and the second conductivity-type nitride semiconductor layers 1455 and 1456, which are provided based on the growth substrate. The buffer layer 1452, for example, may improve crystallinity of the first conductivity-type nitride semiconductor layer 1453 by alleviating a difference in lattice constant between the growth substrate including sapphire and the first conductivity-type nitride semiconductor layer 1453 including gallium nitride.

The buffer layer 1452 may include an undoped semiconductor material. As a non-limiting example, the buffer layer 1452 may include undoped GaN, AlN, InGaN, or the like and may be manufactured at a low temperature of about 500° C. to about 600° C. The buffer layer 1452 may have a thickness of tens to hundreds of angstrom (Å). Here, the buffer layer 1452 being undoped means that the buffer layer 1452 has not undergone a separate impurity doping process. The buffer layer 1452 may include impurities at an intrinsic concentration level even when undoped. For example, when a gallium nitride layer is grown by metal organic chemical vapor deposition (MOCVD), the gallium nitride layer may include Si or the like at a level of about $10^{14}/cm^3$ to about $10^{18}/cm^3$. According to embodiments, the buffer layer 1452 may be omitted in some cases.

The first conductivity-type nitride semiconductor layer 1453 may be arranged on the buffer layer 1452, the active layer 1454 may be arranged on the first conductivity-type nitride semiconductor layer 1453, and the second conductivity-type nitride semiconductor layers 1455 and 1456 may be arranged in the stated order on the active layer 1454.

The first conductivity-type nitride semiconductor layer 1453 may be an n-type nitride semiconductor layer, and each of the second conductivity-type nitride semiconductor layers 1455 and 1456 may be a p-type nitride semiconductor layer. According to some embodiments, the first conductivity-type nitride semiconductor layer 1453 may be a p-type nitride semiconductor layer, and each of the second conductivity-type nitride semiconductor layers 1455 and 1456 may be an n-type nitride semiconductor layer.

According to some embodiments, each of the first conductivity-type nitride semiconductor layer 1453 and the second conductivity-type nitride semiconductor layers 1455 and 1456 may include a material satisfying a compositional formula of $Al_xIn_yGa_{(1-x-y)}N$ (where $0 \le x \le 1$, $0 \le y \le 1$, $0 \le x+y \le 1$). For example, each of the first conductivity-type nitride semiconductor layer 1453 and the second conductivity-type nitride semiconductor layers 1455 and 1456 may include a material such as GaN, AlGaN, InGaN, AlInGaN, or the like. As a non-limiting example, the first conductivity-type nitride semiconductor layer 1453 may include AlGaN doped with an n-type dopant, the second conductivity-type nitride semiconductor layer 1455 may include AlGaN doped with a p-type dopant, and the second conductivity-type nitride semiconductor layer 1456 may include GaN doped with a p-type dopant.

A plurality of the active layer 1454 may be arranged between the first conductivity-type nitride semiconductor layer 1453 and the second conductivity-type nitride semiconductor layers 1455. The plurality of the active layer 1454 may emit light having certain energy by recombination of electrons and holes. Each active layer from among the plurality of the active layer 1454 may include a material having an energy band gap that is less than an energy band gap of each of the first conductivity-type nitride semiconductor layers 1453 and the second conductivity-type nitride semiconductor layer 1455. For example, when each of the first conductivity-type nitride semiconductor layer 1453 and the second conductivity-type nitride semiconductor layer 1455 includes a GaN-based compound semiconductor, each active layer from among the plurality of the active layer 1454 may include an InGaN-based compound semiconductor having an energy band gap that is less than an energy band gap of GaN. According to some embodiments, the plurality of the active layer 1454 may include a multiple quantum well (MQW) structure in which quantum well layers and quantum barrier layers are alternately stacked. According to some embodiments, the plurality of the active layer 1454 may include an alternate stacking structure of InGaN/GaN. However, embodiments of the present disclosure are not limited thereto, and the plurality of the active layer 1454 may include a single quantum well (SQW) structure.

The first electrode 1457 may be a cathode of the LED chip 145. The first electrode 1457 may provide an electrical path with respect to the first conductivity-type nitride semiconductor layer 1453. The first electrode 1457 may contact the first conductivity-type nitride semiconductor layer 1453.

The second electrode 1458 may be an anode of the LED chip 145. The second electrode 1458 may provide an electrical path with respect to the second conductivity-type nitride semiconductor layers 1455 and 1456. The second electrode 1458 may contact the second conductivity-type nitride semiconductor layer 1456.

Each of the first electrode 1457 and the second electrode 1458 may include an Ohmic metal layer, a reflective metal layer, and an under bump metallurgy (UBM) layer.

The Ohmic metal layer may provide Ohmic contact to each of the first conductivity-type nitride semiconductor layer 1453 and the second conductivity-type nitride semiconductor layer 1456. The Ohmic metal layer may include nickel, platinum, gold, and the like.

The reflective metal layer may improve optical efficiency of the LED chip 145 by reflecting UV light generated by the active layer 1454 (or active layers). The reflective metal layer may include at least one metal selected from the group consisting of copper (Cu), aluminum (Al), nickel (Ni), silver (Ag), gold (Au), platinum (Pt), tin (Sn), lead (Pb), titanium (Ti), chromium (Cr), paladium (Pd), indium (In), and zinc (Zn), a metal alloy, carbon (C), and the like.

The UBM layer may include, for example, grooves for coupling to the solders 146 (see FIG. 3). Accordingly, the first electrode 1457 and the second electrode 1458 may respectively contact the solders 146 (see FIG. 3).

Referring again to FIGS. 1 to 3, the waterproof coating layer 150 may cover an upper surface of the substrate 130 and a lateral surface of the LED package 140. The waterproof coating layer 150 may include an encapsulant such as silicone, epoxy, or the like. The waterproof coating layer 150 may isolate the substrate 130, the LED package 140, and an electronic component that is mounted on the substrate 130, from a sterilization-target fluid.

The waterproof coating layer 150 may be provided by a dispensing and spraying process. The waterproof coating layer 150 may include silicone, epoxy, and the like.

According to example embodiments, the waterproof coating layer 150 may cover the lateral surface 141S of the base layer 141 and the lateral surface 147S of the transparent layer 147. According to example embodiments, the waterproof coating layer 150 may cover the entire lateral surface 147S of the transparent layer 147. According to example embodiments, the waterproof coating layer 150 may cover the external connection pads 144 and the external connection solders 148.

According to example embodiments, the waterproof coating layer 150 may expose at least a portion of the upper surface of the LED package 140. According to example embodiments, the waterproof coating layer 150 may not cover the upper surface of the LED package 140.

According to example embodiments, the waterproof coating layer 150 may expose at least a portion of the upper surface 147U of the transparent layer 147. According to example embodiments, the waterproof coating layer 150 may expose the entire upper surface 147U of the transparent layer 147. According to example embodiments, the waterproof coating layer 150 may not cover the upper surface 147U of the transparent layer 147. According to example embodiments, the waterproof coating layer 150 may not contact the upper surface 147U of the transparent layer 147. According to example embodiments, the waterproof coating layer 150 may be apart from the upper surface 147U of the transparent layer 147.

The waterproof coating layer 150 may include a first portion 150P1, which covers the upper surface of the substrate 130, and a second portion 150P2, which covers the lateral surface 141S and the lateral surface 147S of the LED package 140. The first portion 150P1 may contact the upper surface of the substrate 130, and the second portion 150P2 may contact the lateral surface 141S and the lateral surface 147S. As a non-limiting example, the first portion 150P1 may have a conformal shape. The first portion 150P1 may have a constant thickness.

In the present example, the waterproof coating layer 150 may be provided by a dispensing process, a spraying process, an ink-jet process, and the like of a high-viscosity coating material. In the present example, a dynamic viscosity of the coating material for forming the waterproof coating layer 150 may range from about 15000 centipoise (cps) to about 1500000 cps. Accordingly, the second portion 150P2 of the waterproof coating layer 150 may have a convex shape.

According to example embodiments, UV light of the UV light source 100, which has passed through the transparent layer 147, may be directly irradiated onto a sterilization-target fluid such as water, air, and the like without passing through an additional transparent layer. According to example embodiments, the transparent layer 147 may directly contact a sterilization-target fluid such as water, air, and the like.

In UV light sources according to the related art, cover windows such as quartz, glass, and the like cover LED packages such that the LED packages are not exposed to fluids. There is a loss of a large amount of light during the process in which UV light emitted from the LED packages passes through an air layer and a transparent layer.

According to example embodiments, by covering the substrate 130 and the LED package 140 with the waterproof coating layer 150 that does not cover the upper surface 147U of the transparent layer 147, UV light generated by the LED package 140 may be directly transferred to a fluid. Accordingly, a reflection loss generated due to incidence on a cover window and an absorption loss occurring while passing through the cover window may be prevented, and thus, the light extraction efficiency of the UV light source 100 may be improved.

In addition, the upper surface 147U of the transparent layer 147 directly contacts a sterilization-target fluid such as air, water, and the like, and thus, a heat dissipation efficiency of the LED package 140 may be improved.

Table 1 shows operating performances of illumination devices as comparison examples according to the related art and the UV light source 100 according to example embodiments.

TABLE 1

| | Comparison Example 1 | Comparison Example 2 | Experimental Example |
|---|---|---|---|
| Light extraction efficiency | 100 | 97 | 116 |
| Operating temperature (30 mA) | 36.3° C. | 37.5° C. | 33.5° C. |
| Operating temperature (100 mA) | 62.6° C. | 66.7° C. | 53.4° C. |

In Table 1, in the illumination device of Comparison Example 1, an LED package was covered by a cover window, and in the illumination device of Comparison Example 2, an LED chip was directly mounted on a substrate such as a PCB substrate and was covered by a cover window. An illumination device of Experimental Example is substantially the same as the illumination device, that is, the UV light source 100, described with reference to FIGS. 1 to 3.

In Table 1, data regarding light extraction efficiencies is dimensionless values normalized such that the light extraction efficiency of the illumination device of Comparison Example 1 becomes 100. From Table 1, it was confirmed that the light extraction efficiency of the illumination device of Experimental Example was improved by about 16% as compared with the light extraction efficiency of the illumination device of Comparison Example 1. In the case of Comparison Example 2, it was confirmed that the light extraction efficiency was reduced because the LED chip was not packaged by a ceramic substrate or the like.

In the case of being driven by a current of 30 mA, it was confirmed that the operating temperature of the illumination device of Experimental Example was decreased by about 7.7% in terms of Celsius temperature as compared with the operating temperature of the illumination device of Comparison Example 1. In addition, in the case of being driven by a current of 100 mA, it was confirmed that the operating temperature of the illumination device of Experimental Example was decreased by about 14.6% in terms of Celsius temperature as compared with the operating temperature of the illumination device of Comparison Example 1.

In the case of Comparison Example 2, because the LED chip was directly mounted on the substrate such as a PCB substrate, and thus, the heat dissipation efficiency was decreased, it was confirmed that the respective operating temperatures in driving conditions of 30 mA and 100 mA were increased as compared with Comparison Example 1.

From Table 1, it was confirmed that the light extraction efficiency and heat dissipation efficiency of the UV light source 100 according to example embodiments were improved.

The first waterproof layer 161 may be arranged between the waterproof coating layer 150 and the upper housing 120. The first waterproof layer 161 may include, for example, rubber. As the substrate 130 is coupled to the upper housing 120, the waterproof coating layer 150 and the upper housing 120 may apply a certain pressure to the first waterproof layer 161. Accordingly, the first waterproof layer 161 may secure the isolation of the substrate 130 and the LED package 140 from a sterilization-target fluid such as water or the like.

The substrate 130 and the first waterproof layer 161 may be coupled and secured to the upper housing 120 by the securing devices 170.

The second waterproof layer 165 may be arranged between the plate portion 121 of the upper housing 120 and the lower housing 110. The second waterproof layer 165 may contact an outer surface of the sidewall 125. The first waterproof layer 161 may include, for example, rubber. As the lower housing 110 is coupled to the upper housing 120, the lower housing 110 and the upper housing 120 may apply a certain pressure to the second waterproof layer 165. Accordingly, the second waterproof layer 165 may secure the isolation of the substrate 130 and the LED package 140 from a sterilization-target fluid such as water or the like.

The molding layer 180 may be provided onto the lower surface of the substrate 130. The molding layer 180 may include epoxy, silicone, and the like.

The connector 190 may be connected to the substrate 130. The connector 190 may be electrically connected to the LED package 140 via the substrate 130. As a non-limiting example, the substrate 130 may be a double-side wiring substrate and may be electrically connected to each of the LED package 140 arranged on the upper surface thereof and the connector 190 arranged on the lower surface thereof.

Figure 5:
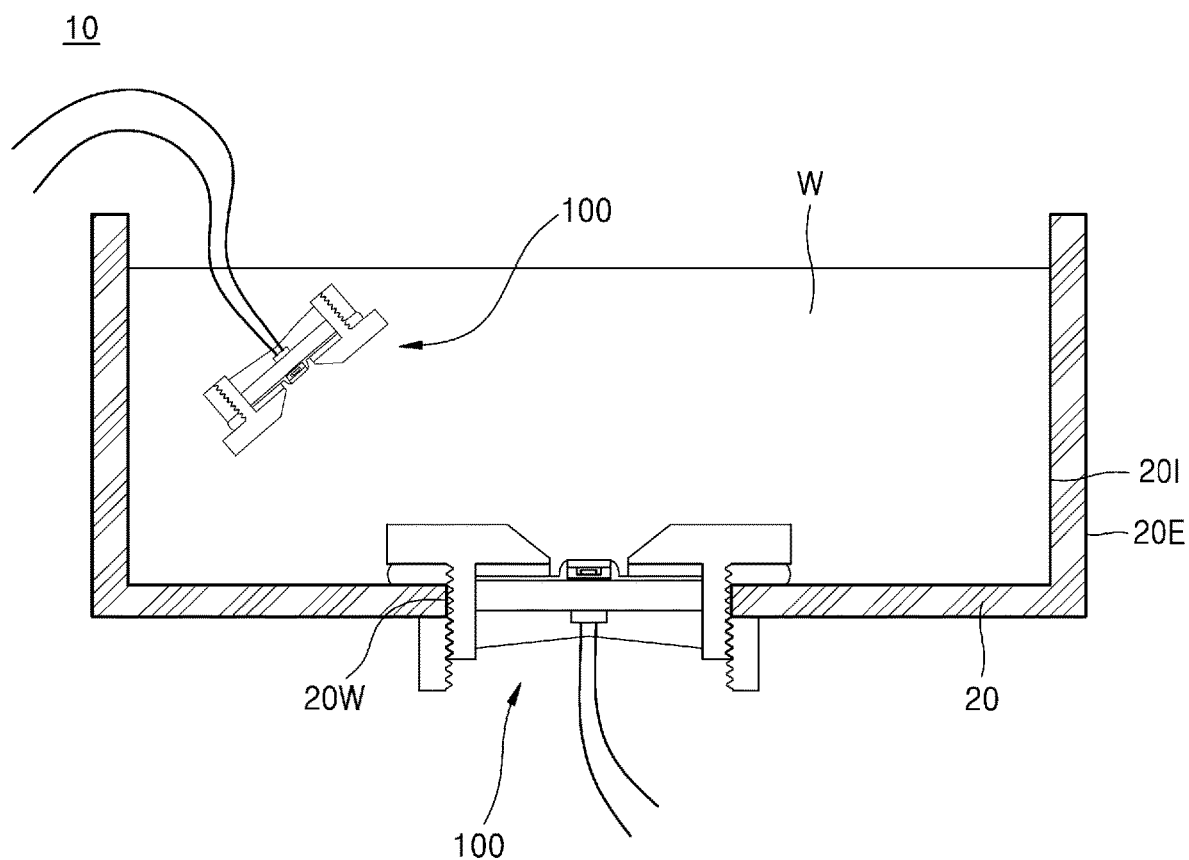
FIG. 5 is a diagram illustrating a water supplier according to example embodiments.

FIG. 5 is a diagram illustrating a water supplier 10 according to example embodiments.

Referring to FIGS. 1 and 5, the water supplier 10 may include a container 20, which stores a fluid such as water W or the like, and the UV light source 100.

The container 20 may store the water W. The water supplier 10 may be configured to supply the water W stored in the container 20 to the outside thereof. According to example embodiments, the container 20 may include an inner wall 20W defining an opening for mounting the UV light source 100. The UV light source 100 coupled to the container 20 may sterilize a fluid such as the water W by irradiating the fluid such as the water W in the container 20 with UV light.

According to example embodiments, one or more of the UV light source 100 may be coupled to the inner wall 20W. According to example embodiments, the lower housing 110 of the UV light source 100 may contact an outer surface 20E of the container 20. According to example embodiments, the second waterproof layer 165 of the UV light source 100 may contact an inner surface 20I of the container 20. According to example embodiments, when the UV light source 100 is installed to the container 20, the second waterproof layer 165 may be arranged between the inner surface 20I of the container 20 and the lower surface of the upper housing 120. According to example embodiments, the second waterproof layer 165 may be pressed by the inner surface 20I of the container 20 and the lower surface of the upper housing 120. Accordingly, the second waterproof layer 165 may prevent a fluid such as the water W from reaching the substrate 130 and the LED package 140 through a space between the inner surface 20I of the container 20 and the lower surface of the upper housing 120. The first waterproof layer 161 may prevent a fluid such as the water W from reaching the substrate 130 and the LED package 140 through a space between the lower surface of the upper housing 120 and the waterproof coating layer 150.

One or more of the UV light source 100 may be provided in the container 20, in which a fluid such as the water W is stored, while being suspended by a wire 191.

Figure 6:
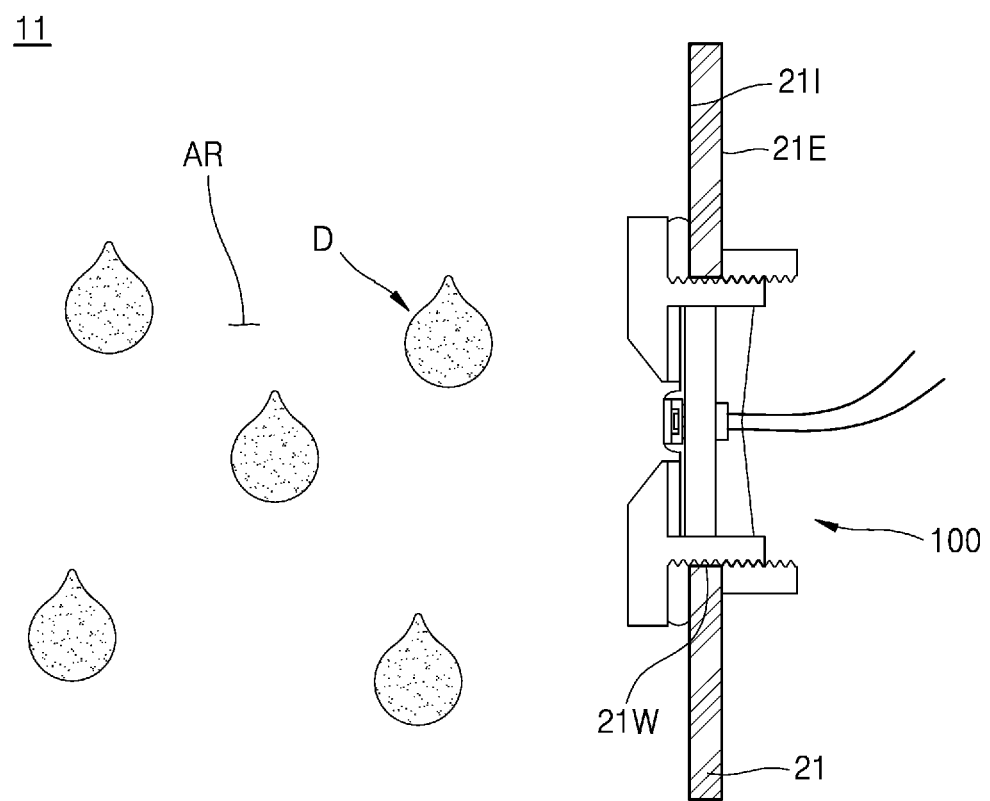
FIG. 6 is a diagram illustrating an air supplier according to example embodiments.

FIG. 6 is a diagram illustrating an air supplier 11 according to example embodiments.

Referring to FIGS. 1 and 6, the air supplier 11 may include a flow path 21, which stores a fluid such as air, and the UV light source 100.

The flow path 21 may provide a path for air AR to move according to an operation of the air supplier 11. There may be water vapor included in the air AR, and dew D caused by condensation of water vapor, inside the flow path 21. According to example embodiments, the UV light source 100 may be coupled to the flow path 21. According to example embodiments, the flow path 21 may include an inner wall 21W defining an opening for mounting the UV light source 100. The UV light source 100 may sterilize a fluid (e.g., the the air AR) by irradiating the fluid in the flow path 21 with UV light.

According to example embodiments, the UV light source 100 may be coupled to the inner wall 21W of the flow path 21. According to example embodiments, the lower housing 110 of the UV light source 100 may contact an outer surface 21E of the flow path 21. According to example embodiments, the second waterproof layer 165 of the UV light source 100 may contact an inner surface 21I of the flow path 21. According to example embodiments, when the UV light source 100 is mounted to the flow path 21, the second waterproof layer 165 may be arranged between the inner surface 21I of the flow path 21 and the lower surface of the upper housing 120. According to example embodiments, the second waterproof layer 165 may be pressed by the inner surface 21I of the flow path 21 and the lower surface of the upper housing 120. Accordingly, the second waterproof layer 165 may prevent a fluid such as the dew D and the air AR from reaching the LED package 140 and the substrate 130 through a space between the inner surface 21I of the flow path 21 and the lower surface of the upper housing 120. The first waterproof layer 161 may prevent a fluid such as the air AR from reaching the substrate 130 and the LED package 140 through a space between the lower surface of the upper housing 120 and the waterproof coating layer 150.

Figure 7A:
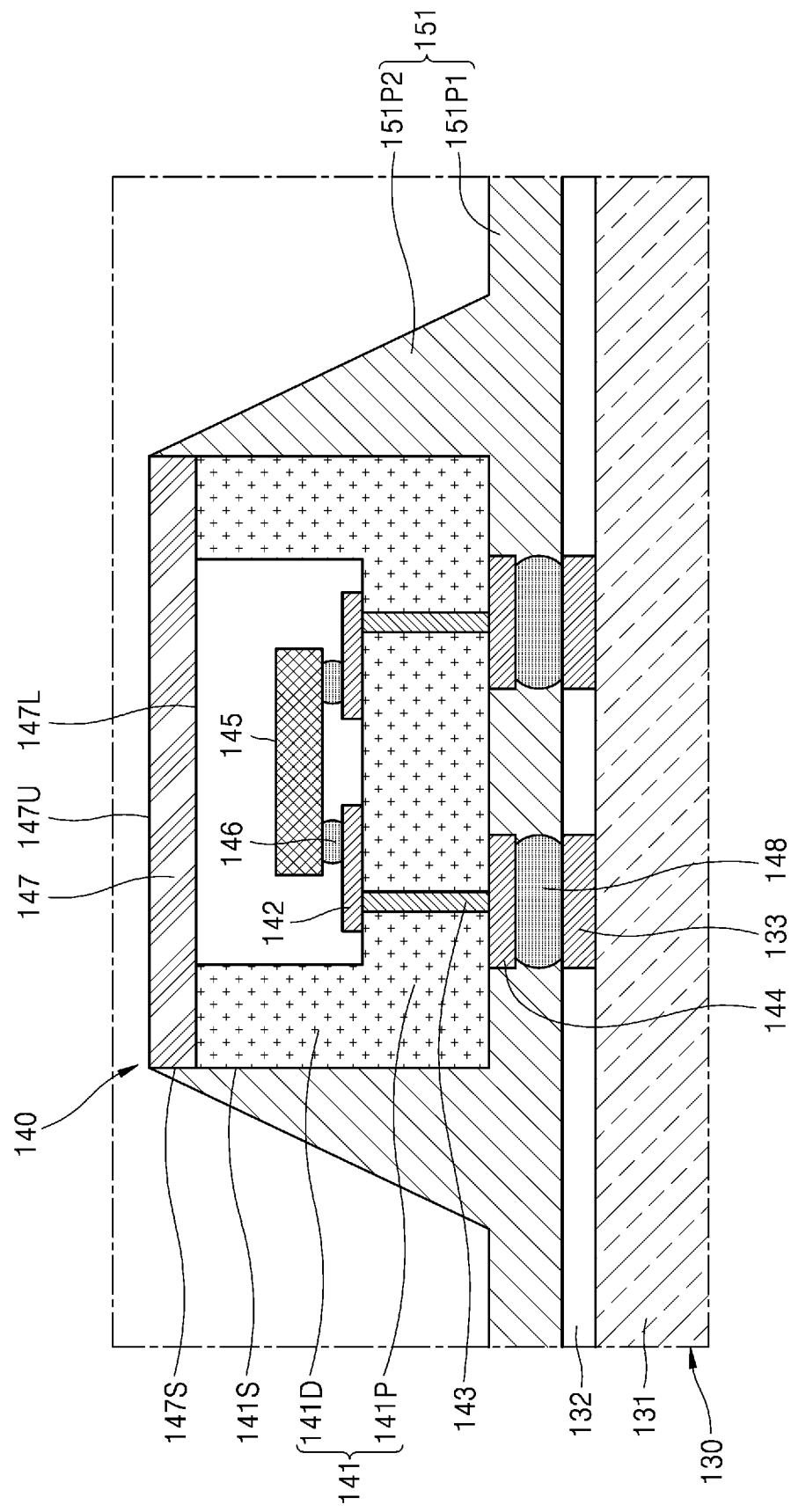
FIG. 7A is a partial cross-sectional view illustrating a portion of a UV light source according to an example embodiment.

FIG. 7A is a partial cross-sectional view illustrating a portion of a UV light source according to other example embodiments and illustrates a portion corresponding to FIG. 3.

Because components shown in FIG. 7A, except for a waterproof coating layer 151, are substantially the same as described with reference to FIG. 3, repeated descriptions thereof are omitted.

Referring to FIG. 7A, the waterproof coating layer 151 may include a first portion 151P1, which covers the upper surface of the substrate 130, and a second portion 151P2, which covers the lateral surface 141S and the lateral surface 147S of the LED package 140. As a non-limiting example, the first portion 151P1 may have a conformal shape. The first portion 151P1 may have a constant thickness.

In the present example, a dynamic viscosity of a coating material for forming the waterproof coating layer 151 may range from about 5000 cps to about 10000 cps. The waterproof coating layer 151 may be provided by a dispensing process, a spraying process, an ink-jet process, and the like of a coating material including silicone, epoxy, and the like. The second portion 151P2 of the waterproof coating layer 151 may include an inclined plane.

Figure 7B:
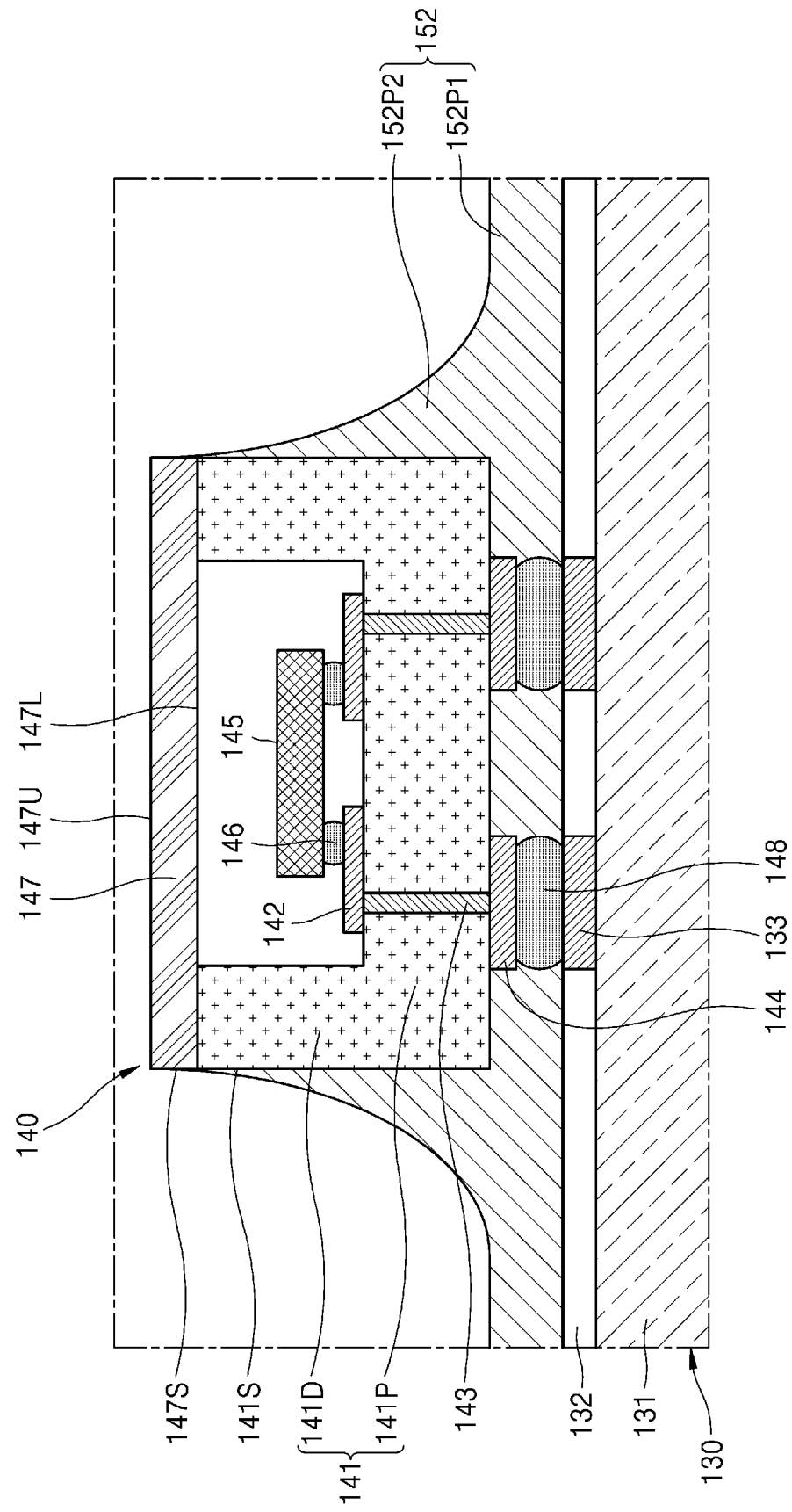
FIG. 7B is a partial cross-sectional view illustrating a portion of a UV light source according to an example embodiment.

FIG. 7B is a partial cross-sectional view illustrating a portion of a UV light source according to other example embodiments and illustrates a portion corresponding to FIG. 3.

Because components shown in FIG. 7B, except for a waterproof coating layer 152, are substantially the same as described with reference to FIG. 3, repeated descriptions thereof are omitted.

Referring to FIG. 7B, the waterproof coating layer 152 may include a first portion 152P1, which covers the upper surface of the substrate 130, and a second portion 152P2, which covers the lateral surface 141S and the lateral surface 147S of the LED package 140. As a non-limiting example, the first portion 152P1 may have a conformal shape. The first portion 152P1 may have a constant thickness.

In the present example, the waterproof coating layer 152 may be provided by a dispensing process, a spraying process, an ink-jet process, and the like of a low-viscosity coating material. In the present example, a dynamic viscosity of a coating material for forming the waterproof coating layer 152 may range from about 1 cps to about 5000 cps. Accordingly, the second portion 152P2 of the waterproof coating layer 152 may have a concave shape. The waterproof coating layer 152 may include silicone, epoxy, and the like.

Figure 7C:
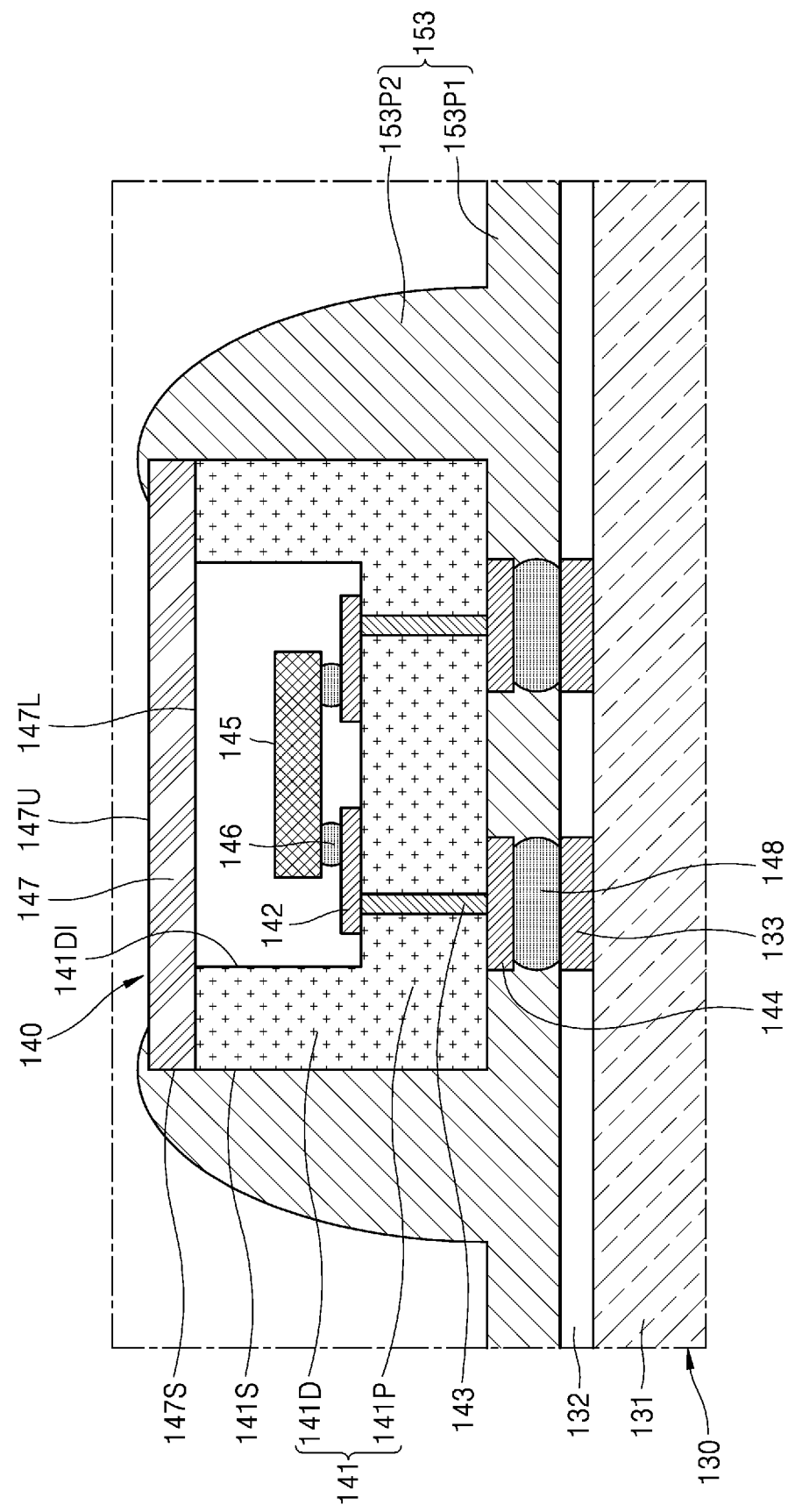
FIG. 7C is a partial cross-sectional view illustrating a portion of a UV light source according to an example embodiment.

FIG. 7C is a partial cross-sectional view illustrating a portion of a UV light source according to other example embodiments and illustrates a portion corresponding to FIG. 3.

Because components shown in FIG. 7C, except for a waterproof coating layer 153, are substantially the same as described with reference to FIG. 3, repeated descriptions thereof are omitted.

Referring to FIG. 7C, the waterproof coating layer 153 may include silicone, epoxy, and the like. The waterproof coating layer 153 may include a first portion 153P1, which covers the upper surface of the substrate 130, and a second portion 153P2, which covers the lateral surface 141S and the lateral surface 147S of the LED package 140. As a non-limiting example, the first portion 153P1 may have a conformal shape. The first portion 153P1 may have a constant thickness.

As a non-limiting example, the second portion 153P2 of the waterproof coating layer 153 may partially cover the upper surface 147U of the transparent layer 147. According to example embodiments, the second portion 153P2 of the waterproof coating layer 153 may cover an edge portion of the upper surface 147U of the transparent layer 147. According to example embodiments, the second portion 153P2 of the waterproof coating layer 153 may contact the edge portion of the upper surface 147U of the transparent layer 147. According to example embodiments, the waterproof coating layer 153 may expose a central portion of the upper surface 147U of the transparent layer 147. According to example embodiments, the waterproof coating layer 153 may be apart from the central portion of the upper surface 147U of the transparent layer 147.

According to example embodiments, a portion of the waterproof coating layer 153, which contacts the upper surface 147U of the transparent layer 147, may overlap the dam portion 141D of the base layer 141 in a vertical direction (for example, a direction that is perpendicular to the upper surface of the substrate 130). According to example embodiments, the portion of the waterproof coating layer 153, which contacts the upper surface 147U of the transparent layer 147, may be apart from an optical path of a luminous flux generated by the LED chip 145. According to example embodiments, the portion of the waterproof coating layer 153, which contacts the upper surface 147U of the transparent layer 147, may be farther from the LED chip 145 in a horizontal direction (for example, a direction that is parallel to the upper surface of the substrate 130) than a distance from the LED chip 145 to an inner surface 141DI of the dam portion 141D of the base layer 141 in the horizontal direction. Accordingly, even though the portion of the waterproof coating layer 153 is arranged on the upper surface 147U of the transparent layer 147, the deterioration of light extraction efficiency of the UV light source may be prevented.

Figure 7D:
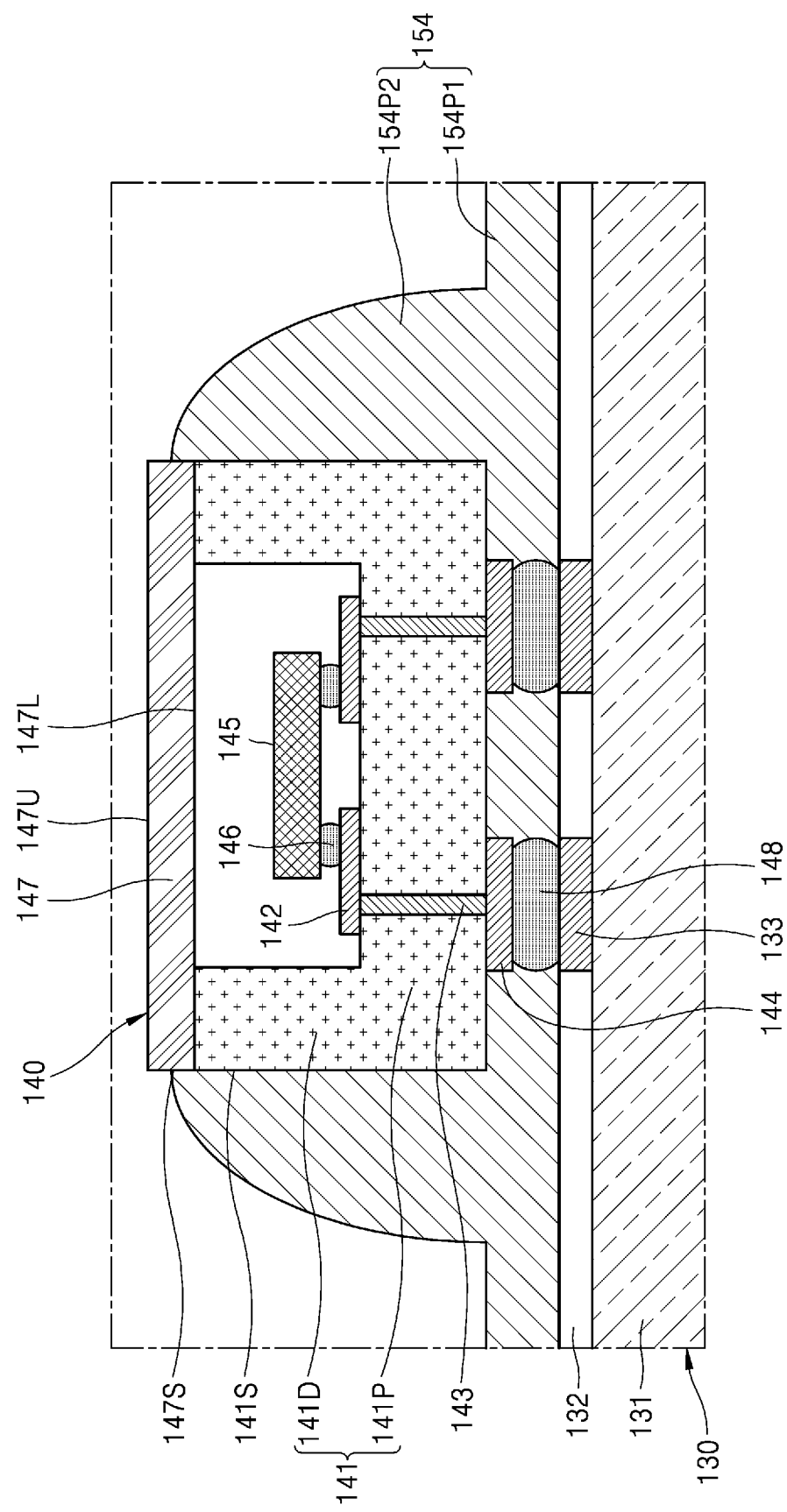
FIG. 7D is a partial cross-sectional view illustrating a portion of a UV light source according to an example embodiment.

FIG. 7D is a partial cross-sectional view illustrating a portion of a UV light source according to other example embodiments and illustrates a portion corresponding to FIG. 3.

Because components shown in FIG. 7D, except for a waterproof coating layer 154, are substantially the same as described with reference to FIG. 3, repeated descriptions thereof are omitted.

Referring to FIG. 7D, the waterproof coating layer 154 may include silicone, epoxy, and the like. The waterproof coating layer 154 may include a first portion 154P1, which covers the upper surface of the substrate 130, and a second portion 154P2, which covers the lateral surface 141S and the lateral surface 147S of the LED package 140. As a non-limiting example, the first portion 154P1 may have a conformal shape. The first portion 154P1 may have a constant thickness.

As a non-limiting example, the second portion 154P2 of the waterproof coating layer 154 may not cover the upper surface 147U of the transparent layer 147. According to example embodiments, the second portion 154P2 of the waterproof coating layer 154 may cover a portion of the lateral surface 147S of the transparent layer 147. According to example embodiments, the second portion 154P2 of the waterproof coating layer 154 may cover a lower portion of the lateral surface 147S of the transparent layer 147 and may not cover an upper portion of the lateral surface 147S of the transparent layer 147. According to example embodiments, the second portion 154P2 of the waterproof coating layer 154 may contact the lower portion of the lateral surface 147S of the transparent layer 147 and may be apart from the upper portion of the lateral surface 147S of the transparent layer 147. According to example embodiments, the second portion 154P2 of the waterproof coating layer 154 covers a bonding portion between the base layer 141 and the transparent layer 147, and thus, waterproofing of the LED package 140 against a sterilization-target fluid may be secured.

Figure 7E:
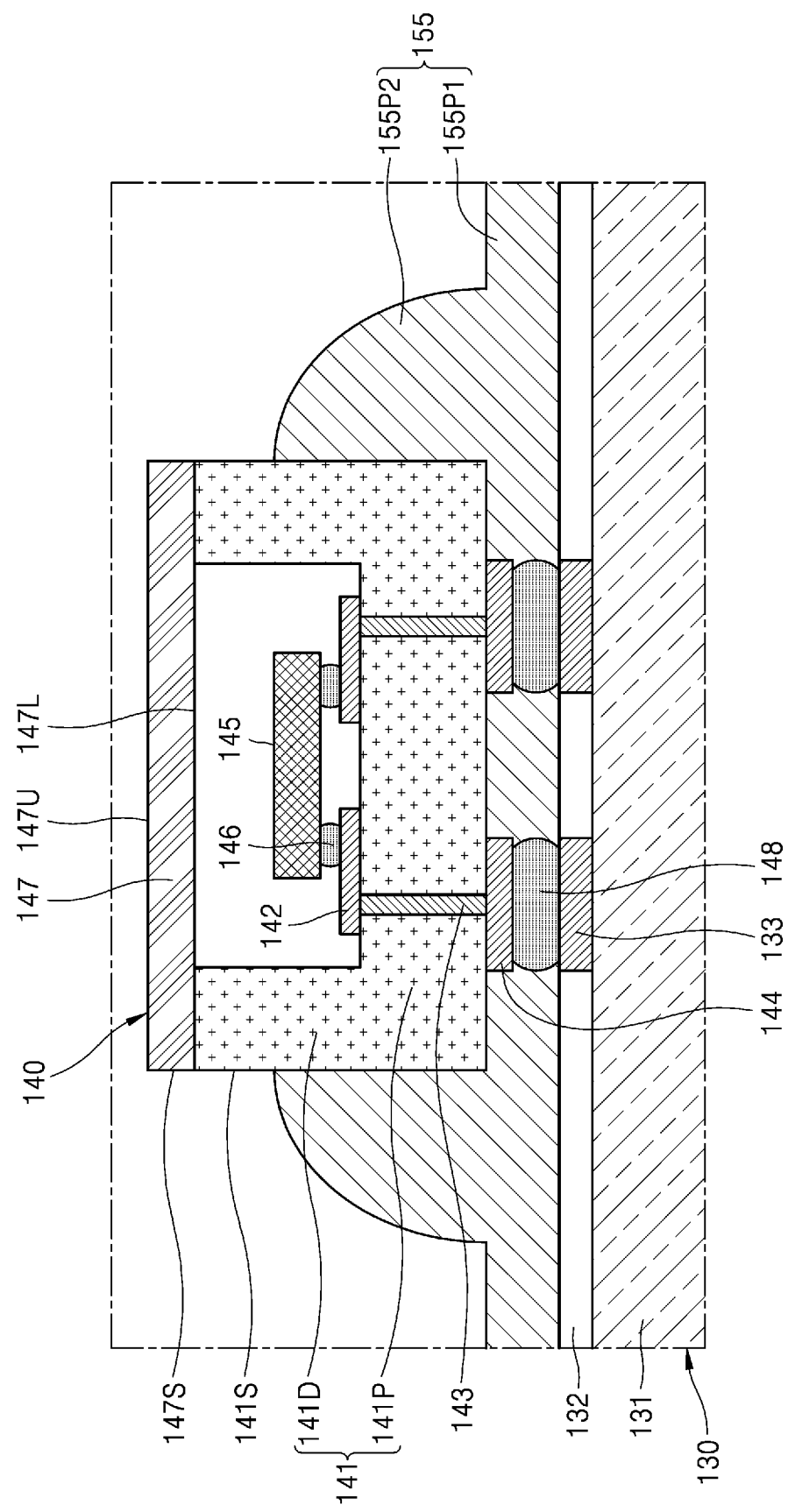
FIG. 7E is a partial cross-sectional view illustrating a portion of a UV light source according to an example embodiment.

FIG. 7E is a partial cross-sectional view illustrating a portion of a UV light source according to other example embodiments and illustrates a portion corresponding to FIG. 3.

Because components shown in FIG. 7E, except for a waterproof coating layer 155, are substantially the same as described with reference to FIG. 3, repeated descriptions thereof are omitted.

Referring to FIG. 7E, the waterproof coating layer 155 may include silicone, epoxy, and the like. The waterproof coating layer 155 may include a first portion 155P1, which covers the upper surface of the substrate 130, and a second portion 155P2, which covers the lateral surface 141S of the LED package 140. As a non-limiting example, the first portion 155P1 may have a conformal shape. The first portion 155P1 may have a constant thickness.

As a non-limiting example, the second portion 155P2 of the waterproof coating layer 155 may not cover the upper surface 147U and the lateral surface 147S of the transparent layer 147. According to example embodiments, the second portion 155P2 of the waterproof coating layer 155 may be apart from the transparent layer 147. According to example embodiments, the waterproof coating layer 155 may partially cover the lateral surface 141S of the base layer 141. According to example embodiments, the waterproof coating layer 155 may cover a lower portion of the lateral surface 141S of the base layer 141 and may not cover an upper portion of the lateral surface 141S of the base layer 141. According to example embodiments, the waterproof coating layer 155 may contact the lower portion of the lateral surface 141S of the base layer 141 and may be apart from the upper portion of the lateral surface 141S of the base layer 141. According to example embodiments, because the base layer 141 is bonded to the transparent layer 147 by a hermetic seal, even when the waterproof coating layer 155 does not cover a border between the base layer 141 and the transparent layer 147, the LED package 140 may provide waterproofing of the LED chip 145.

Figure 7F:
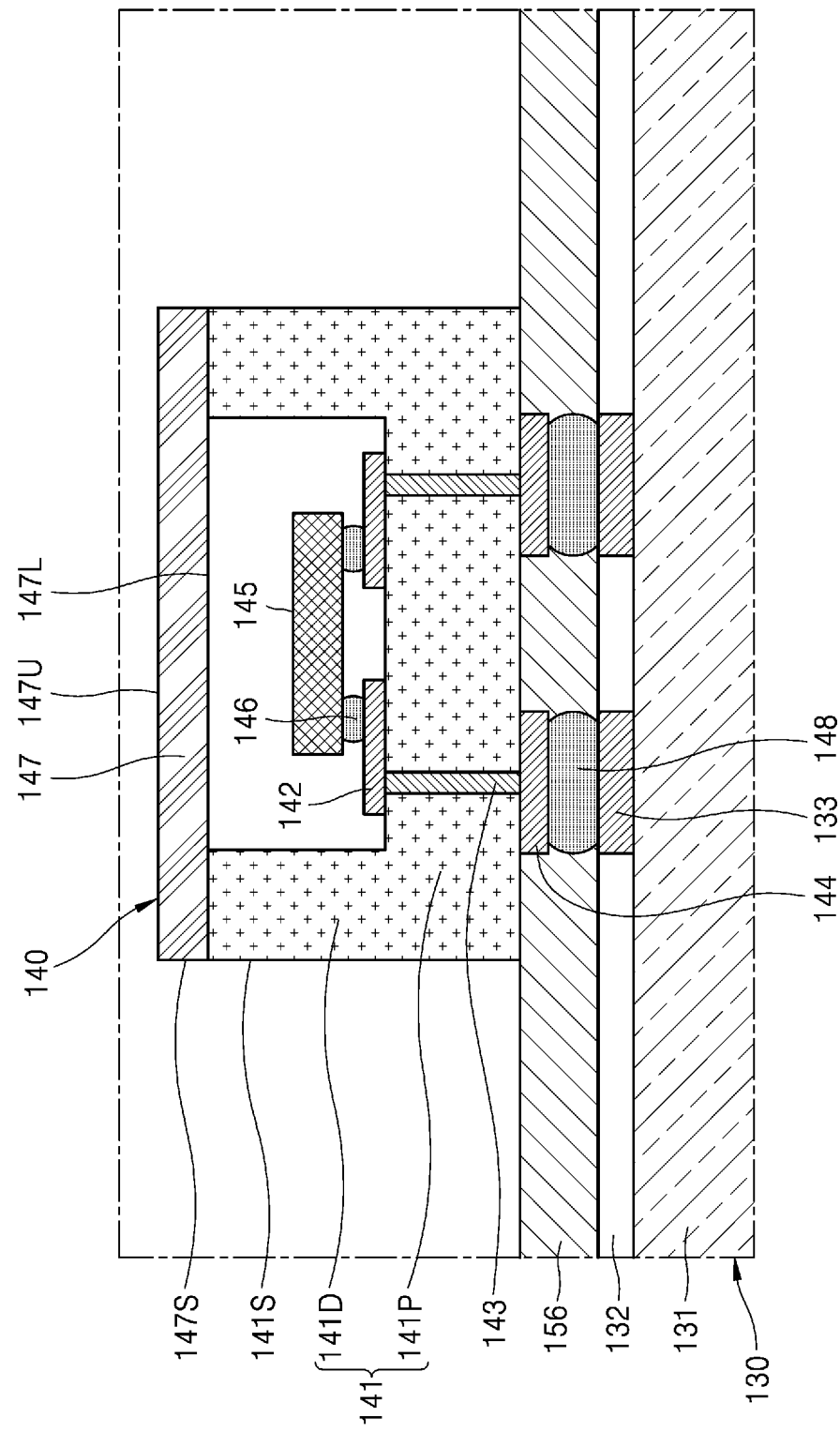
FIG. 7F is a partial cross-sectional view illustrating a portion of a UV light source according to an example embodiment.

FIG. 7F is a partial cross-sectional view illustrating a portion of a UV light source according to other example embodiments and illustrates a portion corresponding to FIG. 3.

Because components shown in FIG. 7F, except for a waterproof coating layer 156, are substantially the same as described with reference to FIG. 3, repeated descriptions thereof are omitted.

Referring to FIG. 7F, the waterproof coating layer 156 may include silicone, epoxy, and the like. The waterproof coating layer 156 may cover the upper surface of the substrate 130. According to example embodiments, the waterproof coating layer 156 may have a conformal shape. According to example embodiments, the waterproof coating layer 156 may have a constant thickness. According to example embodiments, the waterproof coating layer 156 may not cover the lateral surface 141S and the lateral surface 147S of the LED package 140. According to example embodiments, the waterproof coating layer 156 may be apart from the lateral surface 141S and the lateral surface 147S of the LED package 140.

Figure 8A:
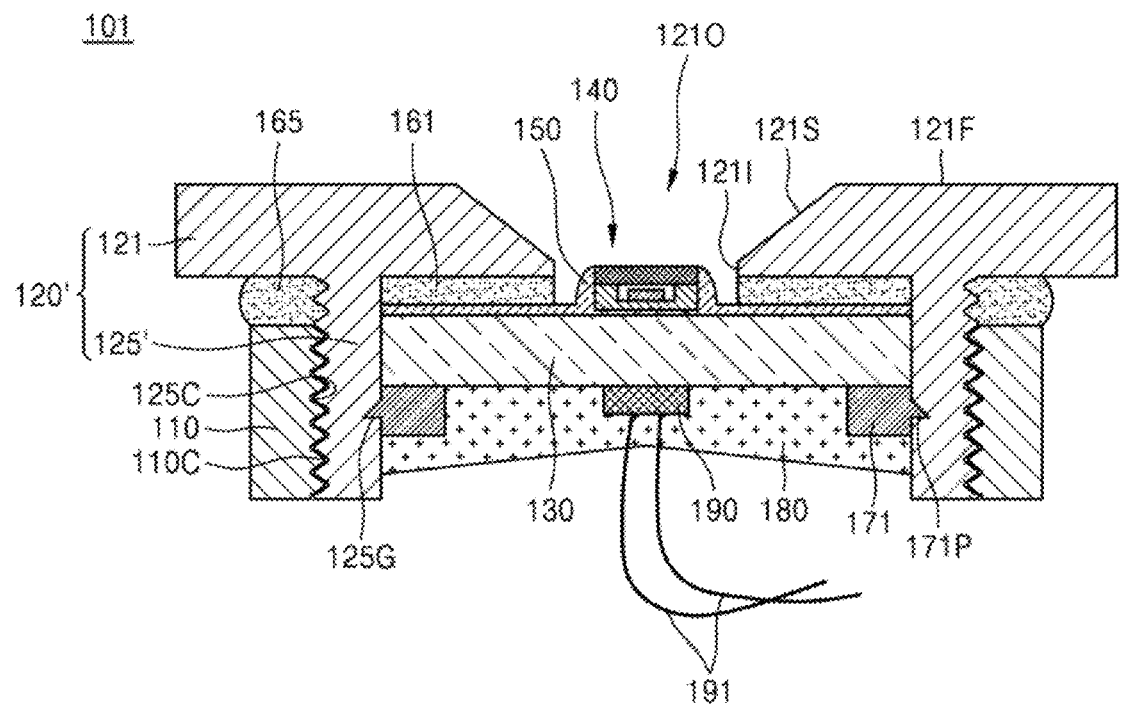
FIG. 8A is a cross-sectional view illustrating a UV light source according to an example embodiment.

FIG. 8A is a cross-sectional view illustrating a UV light source 101 according to other example embodiments.

Referring to FIG. 8A, the UV light source 101 may include the lower housing 110, an upper housing 120', the substrate 130, the LED package 140, the waterproof coating layer 150, the first waterproof layer 161, the second waterproof layer 165, a securing device 171, the molding layer 180, and the connector 190.

Because the lower housing 110, the substrate 130, the LED package 140, the waterproof coating layer 150, the first waterproof layer 161, the second waterproof layer 165, the molding layer 180, and the connector 190 are substantially the same as described with reference to FIGS. 1 to 3, repeated descriptions thereof are omitted.

The upper housing 120' is substantially similar to the upper housing 120 of FIG. 1 except for a groove 125G formed in the sidewall 125'.

According to example embodiments, a securing device 171 may be coupled to the groove 125G of the upper housing 120' and thus secure the substrate 130 and the first waterproof layer 161. According to example embodiments, the securing device 171 may have a ring shape and may include a protrusion 171P for being coupled to the groove 125G in an interference fit manner.

Figure 8B:
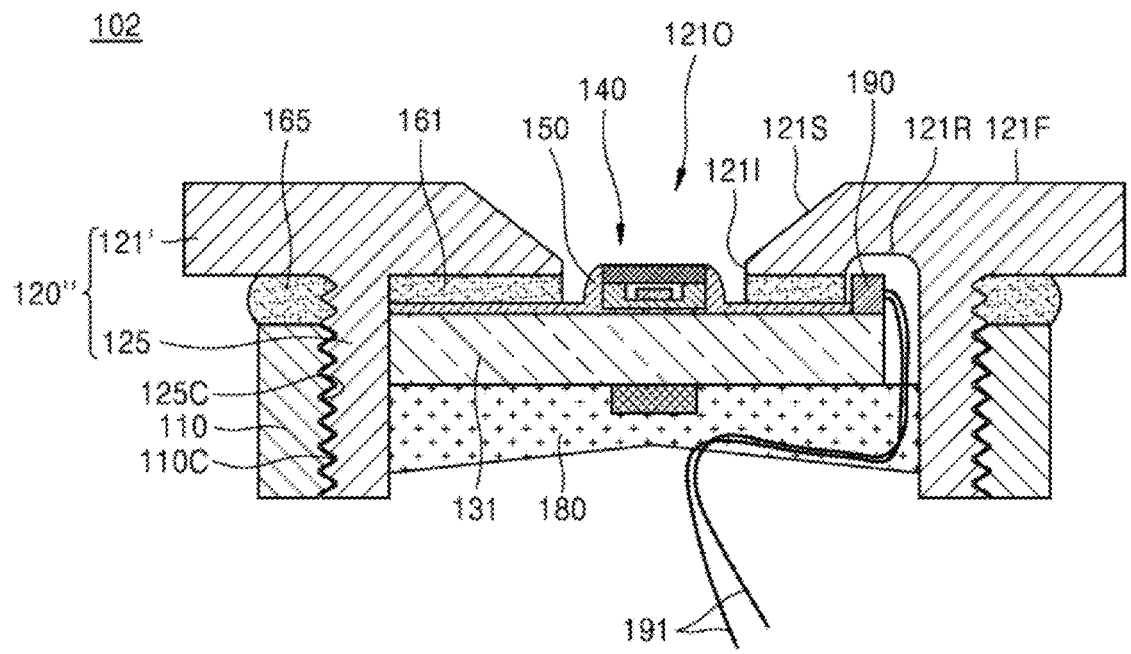
FIG. 8B is a cross-sectional view illustrating a UV light source according to an example embodiment.

FIG. 8B is a cross-sectional view illustrating a UV light source 102 according to other example embodiments.

Referring to FIG. 8B, the UV light source 102 may include the lower housing 110, an upper housing 120", a substrate base 131, the LED package 140, the waterproof coating layer 150, the first waterproof layer 161, the second waterproof layer 165, the molding layer 180, and the connector 190.

Because the lower housing 110, the LED package 140, the waterproof coating layer 150, the first waterproof layer 161, the second waterproof layer 165, the molding layer 180, and the connector 190 are substantially the same as described with reference to FIGS. 1 to 3, repeated descriptions thereof are omitted.

As a non-limiting example, the substrate base 131 may be a single-side PCB. The substrate base 131 may include a circuit pattern formed only on an upper surface thereof, which faces the LED package 140. Each of the LED package 140 and the connector 190 may be arranged on the upper surface of the substrate base 131. The connector 190 may be connected to the LED package 140 via the circuit pattern formed on the upper surface of the substrate base 131.

According to example embodiments, the upper housing 120" may include a plate portion 121' and the sidewall 125.

According to example embodiments, the plate portion 121' is similar to the plate portion 121 of FIG. 1 but may include a recess 121R for accommodating the connector 190.

Figure 8C:
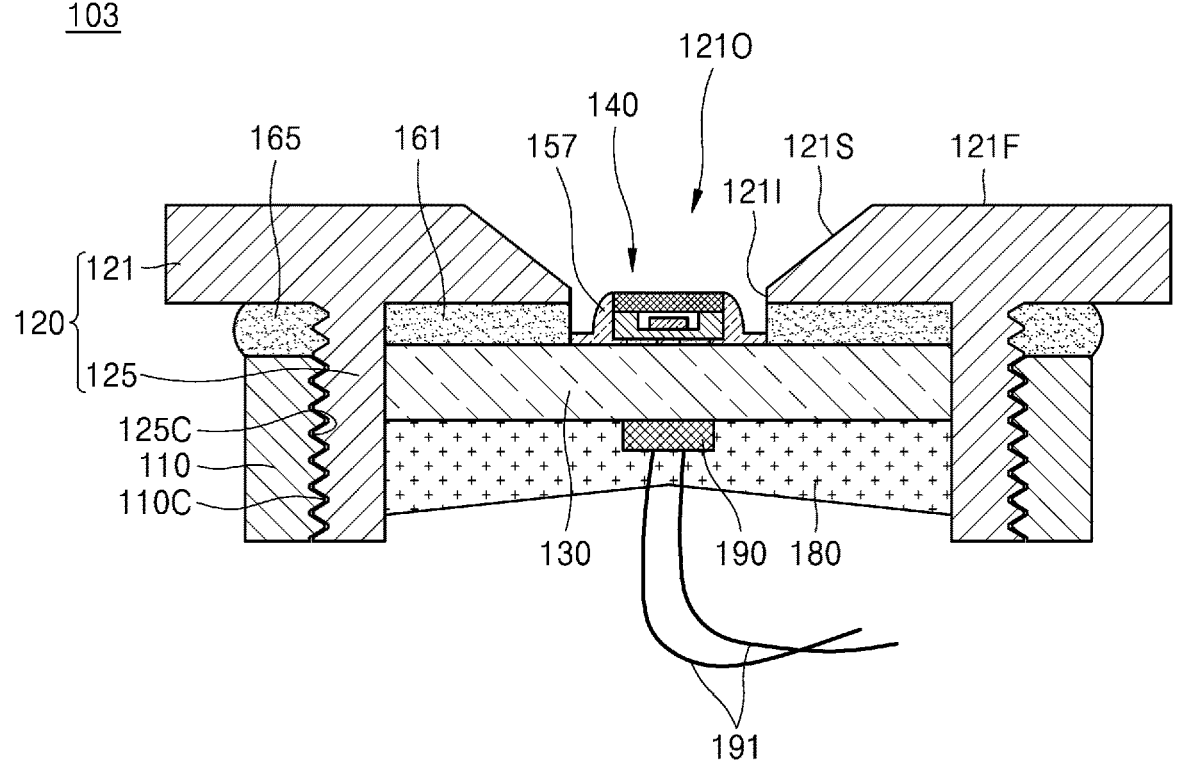
FIG. 8C is a cross-sectional view illustrating a UV light source according to an example embodiment.

FIG. 8C is a cross-sectional view illustrating a UV light source 103 according to other example embodiments.

Referring to FIG. 8C, the UV light source 103 may include the lower housing 110, the upper housing 120, the substrate 130, the LED package 140, a waterproof coating layer 157, the first waterproof layer 161, the second waterproof layer 165, the molding layer 180, and the connector 190.

Because the lower housing 110, the substrate 130, the LED package 140, the first waterproof layer 161, the second waterproof layer 165, the molding layer 180, and the connector 190 are substantially the same as described with reference to FIGS. 1 to 3, repeated descriptions thereof are omitted.

The waterproof coating layer 157 may include silicone, epoxy, and the like. According to example embodiments, the waterproof coating layer 157 may cover a portion of the upper surface of the substrate 130. According to example embodiments, the waterproof coating layer 157 may cover a central portion of the upper surface of the substrate 130 and may not cover an edge portion of the upper surface of the substrate 130.

According to example embodiments, the waterproof coating layer 157 may not be arranged between the plate portion 121 of the upper housing 120 and the upper surface of the substrate 130. According to example embodiments, only the first waterproof layer 161 may be arranged between the plate portion 121 of the upper housing 120 and the upper surface of the substrate 130. According to example embodiments, the upper surface of the first waterproof layer 161 may contact the plate portion 121 of the upper housing 120, and the lower surface of the first waterproof layer 161 may contact the substrate 130.

According to example embodiments, the waterproof coating layer 157 may not contact the lower surface of the first waterproof layer 161. According to example embodiments, the waterproof coating layer 157 may be apart from the lower surface of the first waterproof layer 161.

According to example embodiments, the waterproof coating layer 157 may cover only a portion of the upper surface of the substrate 130, the portion being exposed by the opening 121O of the upper housing 120. According to example embodiments, the upper surface of the substrate 130 may be covered by the waterproof coating layer 157 and the first waterproof layer 161. According to example embodiments, the upper surface of the substrate 130 may be covered by one of the waterproof coating layer 157 and the first waterproof layer 161. According to example embodiments, a portion of the upper surface of the substrate 130 may be covered by the waterproof coating layer 157, and another portion of the upper surface of the substrate 130 may be covered by the first waterproof layer 161.

According to example embodiments, the waterproof coating layer 157 is provided onto only the portion of the upper surface of the substrate 130, which is not covered by the first waterproof layer 161, and thus, the productivity of the UV light source 103 may be improved.

Figure 8D:
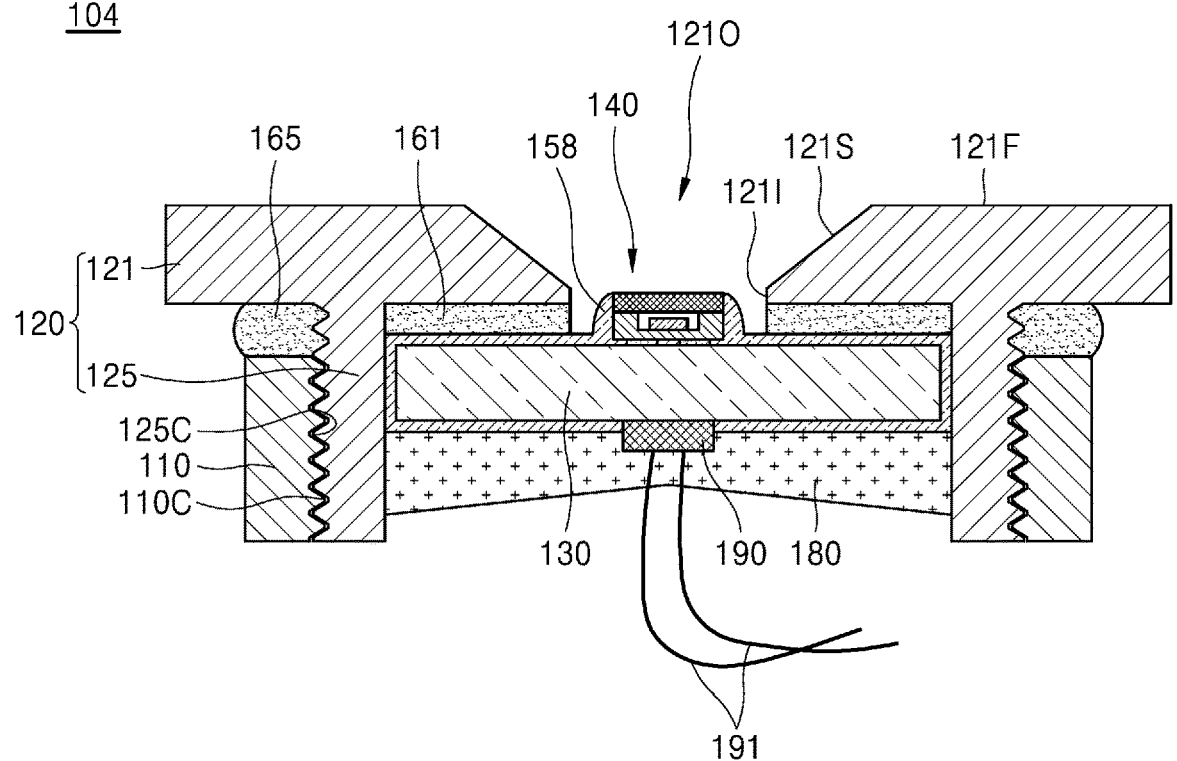
FIG. 8D is a cross-sectional view illustrating a UV light source according to an example embodiment.

FIG. 8D is a cross-sectional view illustrating a UV light source 104 according to other example embodiments.

Referring to FIG. 8D, the UV light source 104 may include the lower housing 110, the upper housing 120, the substrate 130, the LED package 140, a waterproof coating layer 158, the first waterproof layer 161, the second waterproof layer 165, the molding layer 180, and the connector 190.

Because the lower housing 110, the substrate 130, the LED package 140, the first waterproof layer 161, the second waterproof layer 165, the molding layer 180, and the connector 190 are substantially the same as described with reference to FIGS. 1 to 3, repeated descriptions thereof are omitted.

The waterproof coating layer 158 may include silicone, epoxy, and the like. According to example embodiments, the waterproof coating layer 158 may cover the upper surface, a lateral surface, and the lower surface of the substrate 130. According to example embodiments, the waterproof coating layer 158 may coat the entire substrate 130.

Accordingly, the waterproof coating layer 158 may include a portion arranged between the first waterproof layer 161 and the substrate 130, a portion arranged between the sidewall 125 of the upper housing 120 and the substrate 130, and a portion arranged between the substrate 130 and the molding layer 180.

According to example embodiments, the waterproof coating layer 158 covers the entire substrate 130, and thus, the waterproofing performance of the UV light source 104 may be further improved.

Figure 9:
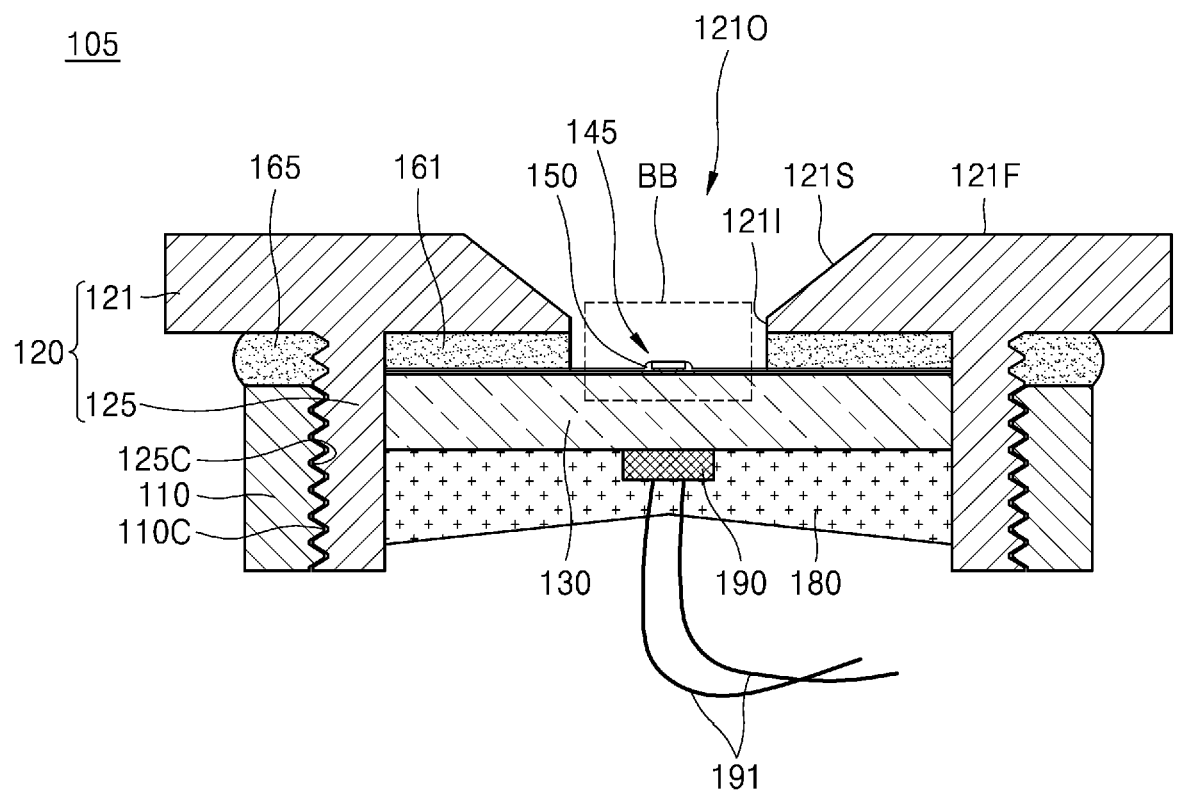
FIG. 9 is a cross-sectional view of a UV light source according to example embodiments.

FIG. 9 is a cross-sectional view illustrating a UV light source 105 according to example embodiments.

Figure 10:
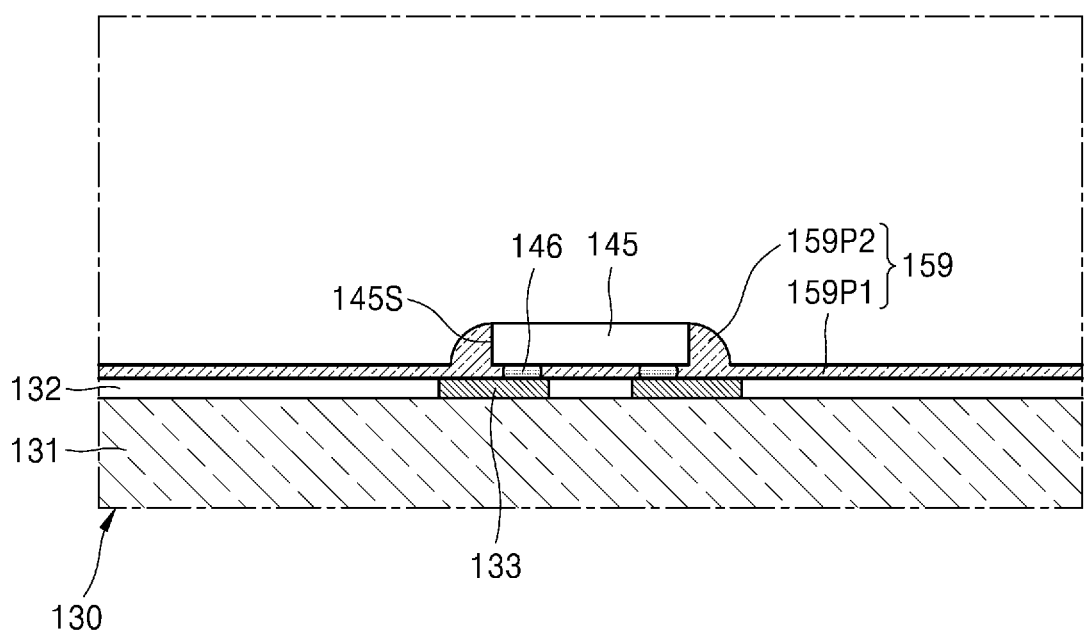
FIG. 10 is a partially enlarged cross-sectional view of a region BB of FIG. 9.

FIG. 10 is a partially enlarged cross-sectional view of a region BB of FIG. 9.

Referring to FIGS. 9 and 10, the UV light source 105 may include the lower housing 110, the upper housing 120, the substrate 130, the LED chip 145, a waterproof coating layer 159, the first waterproof layer 161, the second waterproof layer 165, the molding layer 180, and the connector 190.

Because the lower housing 110, the substrate 130, the first waterproof layer 161, the second waterproof layer 165, the molding layer 180, and the connector 190 are substantially the same as described with reference to FIGS. 1 to 3, repeated descriptions thereof are omitted.

The LED chip 145 may be mounted directly on the substrate 130. The LED chip 145 may have a thickness of about 100 nm to about 700 nm. As a non-limiting example, the LED chip 145 may be coupled to the pads 133 via the solders 146. The LED chip 145 may be coupled to the pads 133 by eutectic bonding and the solders 146 may be omitted.

The waterproof coating layer 159 may include silicone, epoxy, and the like. The waterproof coating layer 159 may include a first portion 159P1, which covers the upper surface of the substrate 130, and a second portion 159P2, which covers the lateral surface 145S of the LED chip 145. The first portion 159P1 of the waterproof coating layer 159 may contact the upper surface of the substrate 130. The second portion 159P2 of the waterproof coating layer 159 may contact the lateral surface 145S of the LED chip 145. According to example embodiments, the waterproof coating layer 159 may further cover the solders 146.

According to example embodiments, the LED chip 145 is mounted directly on the substrate 130, and thus, light having passed through the transparent layer 145l (see FIG. 4) of the LED chip 145 may be directly transferred to a sterilization-target fluid such as water without passing through a transparent layer (e.g., a transparent layer 147 of FIG. 3) of an LED package. In addition, the cost and time required for packaging the LED chip 145 may be reduced, and thus, the productivity of the UV light source 105 may be improved.

Those of ordinary skill in the art would also recognize, based on the descriptions made herein, that the present disclosure also includes an embodiment where the waterproof coating layer 159 includes only the first portion 159P1 covering the upper surface of the substrate 130, an embodiment where the second portion 159P2 of the waterproof coating layer 159 has a straight slope, and an embodiment where the second portion 159P2 of the waterproof coating layer 159 has a concave shape.

Figure 11:
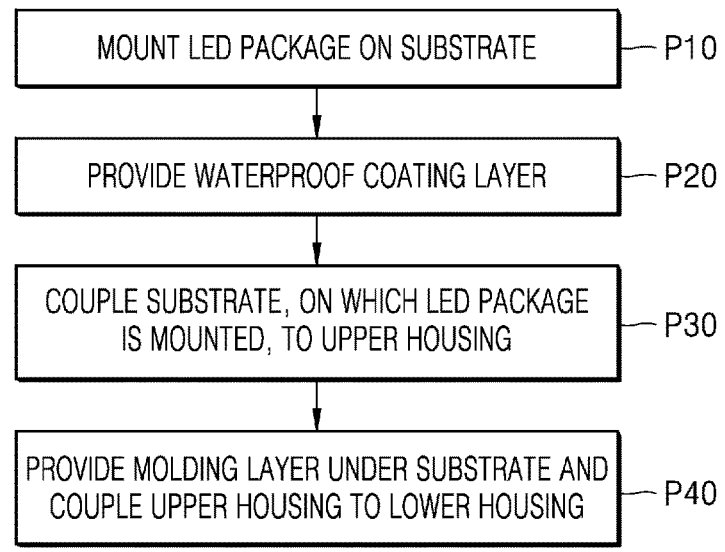
FIG. 11 is a flowchart illustrating a method of manufacturing a UV light source, according to example embodiments.

FIG. 11 is a flowchart illustrating a method of manufacturing a UV light source, according to example embodiments.

Figure 12A:
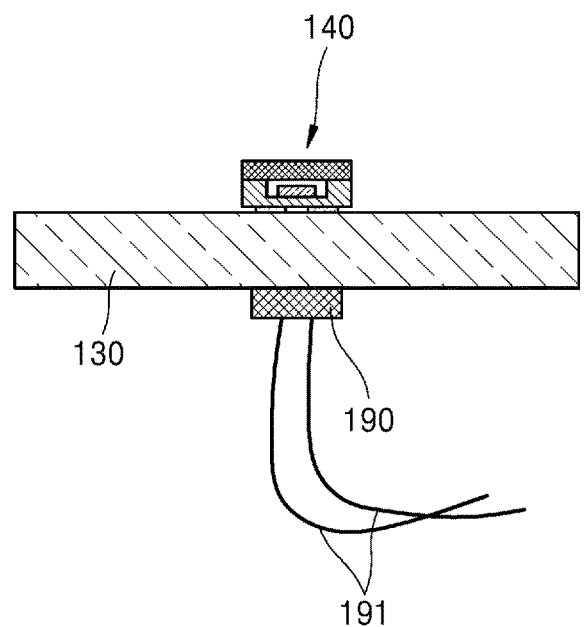
FIG. 12A is a first diagram illustrating a method of manufacturing a UV light source, according to example embodiments.
Figure 12B:
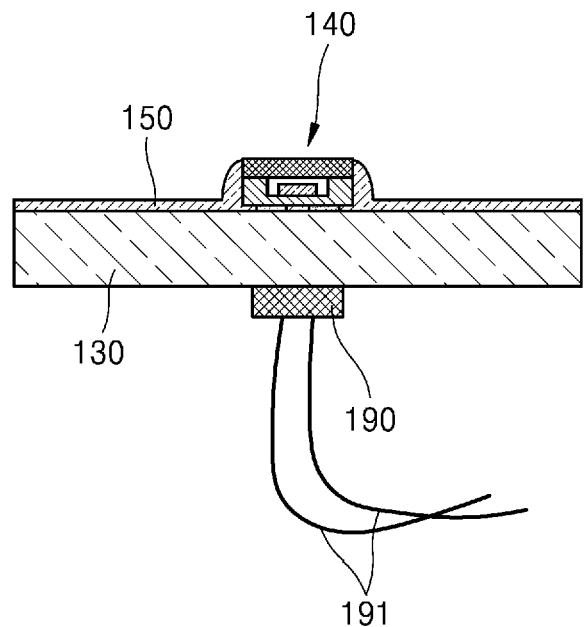
FIG. 12B is a second diagram illustrating the method of manufacturing the UV light source, according to example embodiments.
Figure 12C:
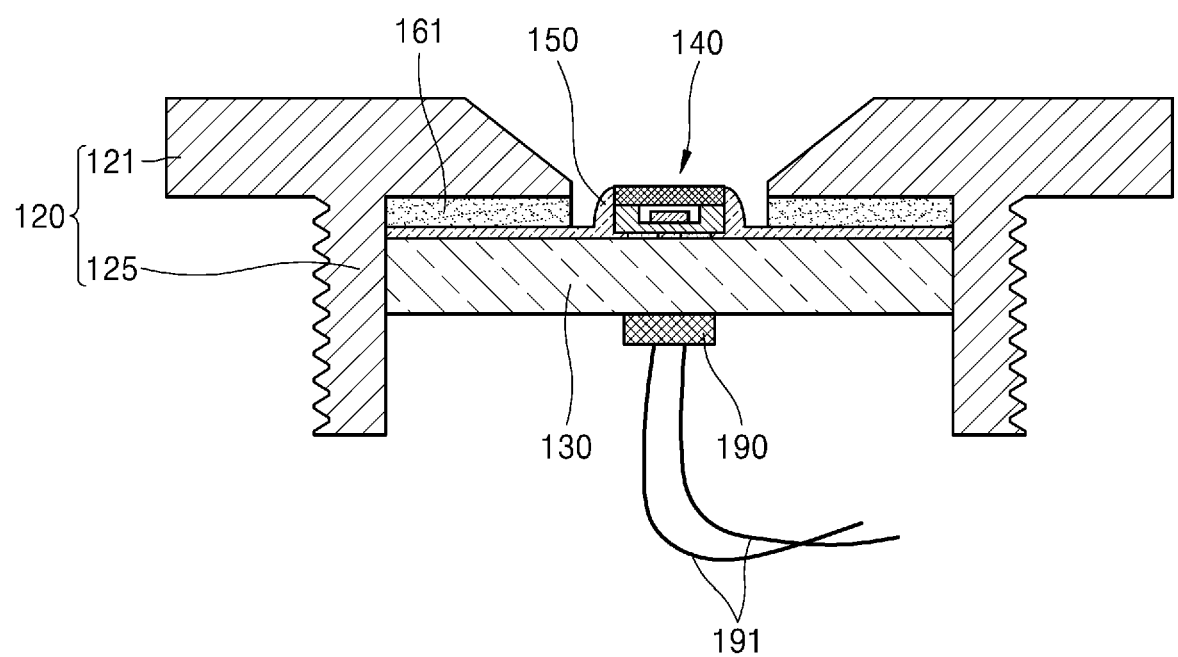
FIG. 12C is a third diagram illustrating the method of manufacturing the UV light source, according to example embodiments.

FIGS. 12A to 12C are diagrams illustrating a method of manufacturing a UV light source, according to example embodiments.

Referring to FIGS. 11 and 12A, in P10, the LED package 140 may be mounted on the substrate 130. According to example embodiments, passive elements such as a resistor and a capacitor may be further mounted on the substrate 130. The LED package 140 and the additional passive elements may be coupled to the substrate 130 by a surface mounting technique. According to example embodiments, the connector 190 including the wire 191 may be connected to the substrate 130.

Next, referring to FIGS. 11 and 12B, in P20, the waterproof coating layer 150 may be provided. Providing the waterproof coating layer 150 may include providing a coating material including silicone, epoxy, and the like by a dispensing and spraying process, and curing the coating material. The coating material may be cured by one of UV curing and thermal curing. The waterproof coating layer 150 may cover the upper surface of the substrate 130 and the lateral surface of the LED package 140.

Next, referring to FIGS. 11 and 12C, in P30, the substrate 130 on which the LED package 140 is mounted may be coupled to the upper housing 120. When the substrate 130 is coupled to the upper housing 120, the first waterproof layer 161 may be arranged therebetween. The substrate 130 may be secured to the upper housing 120 by at least one of the securing devices 170 (see FIG. 2). The substrate 130 may be secured to the upper housing 120 while being located to press the first waterproof layer 161.

Next, referring to FIGS. 11 and 1, in P40, the molding layer 180 may be provided under the substrate 130, and the upper housing 120 may be coupled to the lower housing 110. When the upper housing 120 is coupled to the lower housing 110, the second waterproof layer 165 may be arranged therebetween. The upper housing 120 and the lower housing 110 may be secured to each other while being located to press the second waterproof layer 165.

While non-limiting example embodiments of the present disclosure have been particularly shown and described, it will be understood that various changes in form and details may be made to embodiments of the present disclosure without departing from the spirit and scope of the present disclosure.

What is claimed is:

1. An ultraviolet (UV) light source comprising:
    a lower housing;
    an upper housing coupled to the lower housing, the upper housing comprising a first plate portion and a sidewall protruding from the first plate portion;
    a substrate coupled to the upper housing;
    a light-emitting diode (LED) package on the substrate;
    a waterproof coating layer on at least a portion of the substrate; and
    a first waterproof layer between the waterproof coating layer and the upper housing, wherein the LED package comprises:
        an LED chip configured to generate UV light; and
        a transparent layer comprising a lower surface facing the LED chip, an upper surface opposite to the lower surface, and a lateral surface connecting the upper surface to the lower surface,
    wherein at least a portion of the upper surface of the transparent layer is exposed from the waterproof coating layer,
    wherein the transparent layer is configured to directly contact a sterilization-target fluid, and
    wherein the waterproof coating layer is on the lateral surface of the transparent layer.

2. The UV light source of claim 1, wherein the LED package further comprises a base layer comprising a second plate portion, on which the LED chip is mounted, and a dam portion, which protrudes from the second plate portion of the LED package and contacts the transparent layer.

3. The UV light source of claim 2, wherein the waterproof coating layer is on a lateral surface of the base layer.

4. The UV light source of claim 2, wherein the waterproof coating layer is apart from a lateral surface of the base layer.

5. The UV light source of claim 2, wherein the base layer is coupled to the transparent layer by a hermetic seal.

6. The UV light source of claim 1, wherein the waterproof coating layer is on another portion of the upper surface of the transparent layer.

7. The UV light source of claim 6, wherein the waterproof coating layer is on the other portion of the upper surface of the transparent layer, without being on the portion of the upper surface of the transparent layer, such that the LED chip is configured to generate a luminous flux that passes through the transparent layer and does not pass through the waterproof coating layer.

8. The UV light source of claim 1, wherein the waterproof coating layer is on an edge portion of the upper surface of the transparent layer.

9. The UV light source of claim 1, wherein the waterproof coating layer is apart from the upper surface of the transparent layer.

10. The UV light source of claim 1, wherein the waterproof coating layer comprises at least one from among silicone and epoxy.

11. The UV light source of claim 1, wherein the LED chip is configured to generate a wavelength of light that is equal to or greater than 100 nm and equal to or less than 280 nm.

12. An ultraviolet (UV) light source comprising:
    an upper housing comprising a plate portion and a sidewall protruding from the plate portion;
    a substrate coupled to the upper housing;
    a light-emitting diode (LED) chip on the substrate and comprising a transparent layer;
    a waterproof coating layer on the substrate and at least a portion of the LED chip; and
    a first waterproof layer between the waterproof coating layer and the upper housing,
    wherein at least a portion of an upper surface of the transparent layer is exposed from the waterproof coating layer, such that the LED chip is configured to generate UV light that is directly transferred to a sterilization-target fluid without passing through the waterproof coating layer, and
    wherein the waterproof coating layer is on a lateral surface of the transparent layer.

13. The UV light source of claim 12, wherein a thickness of the LED chip is equal to or greater than 100 μm and equal to or less than 700 μm.

14. The UV light source of claim 12, wherein the waterproof coating layer comprises:
    a first portion on the substrate; and
    a second portion on a lateral surface of the LED chip.

15. The UV light source of claim 14, wherein the LED chip further comprises:
    a first conductivity-type nitride semiconductor layer on the transparent layer;
    an active layer on the first conductivity-type nitride semiconductor layer; and
    a second conductivity-type nitride semiconductor layer on the active layer, and
    wherein the second portion of the waterproof coating layer is not on the upper surface of the transparent layer.

16. An ultraviolet (UV) light source comprising:
an upper housing comprising a first plate portion and a sidewall protruding from the first plate portion;
a substrate coupled to the upper housing;
a light-emitting diode (LED) package mounted on an upper surface of the substrate and comprising an LED chip configured to generate UV light;
a waterproof coating layer on at least a portion of the upper surface of the substrate;
a first waterproof layer between the waterproof coating layer and the upper housing; and
a connector connected to the substrate and providing a path for drive power to the LED chip,
wherein the LED package further comprises:
a base layer comprising a second plate portion, which is overlapped with a lower surface of the LED chip, and a dam portion, which is overlapped with a lateral surface of the LED chip; and
a transparent layer on the dam portion of the base layer, the transparent layer comprising a lower surface facing the LED chip, an upper surface opposite to the lower surface of the transparent layer, and a lateral surface connecting the upper surface of the transparent layer to the lower surface of the transparent layer,
wherein the waterproof coating layer is on the lateral surface of the transparent layer.

17. The UV light source of claim 16, wherein the waterproof coating layer comprises:
a first portion on the substrate; and
a second portion on the LED package, and
wherein the second portion of the waterproof coating layer has a convex shape.

18. The UV light source of claim 16, wherein the waterproof coating layer comprises:
a first portion on the substrate; and
a second portion on the LED package, and
wherein the second portion of the waterproof coating layer comprises an inclined plane.

* * * * *